(12) United States Patent
Iantorno et al.

(10) Patent No.: US 9,679,114 B2
(45) Date of Patent: Jun. 13, 2017

(54) SYSTEMS AND METHODS FOR DISPENSING PRESCRIPTION MEDICATION USING A MEDICATION DISPENSING MACHINE

(71) Applicant: Medifriend, Inc., Solana Beach, CA (US)

(72) Inventors: Pat P. Iantorno, San Francisco, CA (US); Stefan Kanetis, Del Mar, CA (US)

(73) Assignee: MediFriend, Inc., Solana Beach, CA (US)

( * ) Notice: Subject to any disclaimer, the term of this patent is extended or adjusted under 35 U.S.C. 154(b) by 0 days.

(21) Appl. No.: 14/298,194

(22) Filed: Jun. 6, 2014

(65) Prior Publication Data

US 2014/0361076 A1    Dec. 11, 2014

Related U.S. Application Data

(60) Provisional application No. 61/832,151, filed on Jun. 7, 2013.

(51) Int. Cl.
   *G06F 19/00*  (2011.01)
   *G07F 17/00*  (2006.01)

(52) U.S. Cl.
   CPC ...... *G06F 19/3462* (2013.01); *G07F 17/0092* (2013.01)

(58) Field of Classification Search
   CPC .................. G06F 19/3462; G07F 17/0092
   USPC .......................................... 235/381
   See application file for complete search history.

(56) References Cited

U.S. PATENT DOCUMENTS

| | | |
|---|---|---|
| 3,624,792 A | 11/1971 | Ernest |
| 4,411,351 A | 10/1983 | Lowder et al. |
| 5,468,110 A | 11/1995 | McDonald et al. |
| 5,561,604 A | 10/1996 | Buckley et al. |
| 5,593,267 A | 1/1997 | McDonald et al. |
| 6,152,364 A | 11/2000 | Schoonen et al. |
| 6,230,927 B1 | 5/2001 | Schoonen et al. |
| 6,352,200 B1 | 3/2002 | Schoonen et al. |
| 6,529,801 B1 | 3/2003 | Rosenblum |

(Continued)

FOREIGN PATENT DOCUMENTS

JP   2011-194030 A   10/2011

OTHER PUBLICATIONS

International Search Report and Written Opinion for related application No. PCT/US2014/041400, mailed on Oct. 2, 2014, 10 pages.

*Primary Examiner* — Toan Ly
(74) *Attorney, Agent, or Firm* — Vander Velden Law Firm, LLC

(57) ABSTRACT

Systems and methods for dispensing prescription medication from a medication-dispensing machine. In an embodiment, an identification of medication and patient information for an electronic prescription is received. A container of the identified medication is retrieved from a plurality of containers stocked within the machine. Each container comprises a first barcode. The first barcode is scanned, and a patient label is generated and applied to the retrieved container. An image of the retrieved container is captured and provided to a pharmacist over a network. After an approval is received over the network from the pharmacist, the retrieved container is released to a user.

20 Claims, 20 Drawing Sheets

(56) References Cited

U.S. PATENT DOCUMENTS

| | | |
|---|---|---|
| 6,892,941 B2 | 5/2005 | Rosenblum |
| 6,929,149 B2 | 8/2005 | Selfridge et al. |
| 7,063,232 B2 | 6/2006 | Chirnomas |
| 7,251,546 B2 | 7/2007 | Chirnomas |
| 7,334,701 B2 | 2/2008 | Chirnomas et al. |
| 7,407,064 B2 | 8/2008 | Chirnomas |
| 7,444,203 B2 | 10/2008 | Rosenblum |
| 7,469,820 B2 | 12/2008 | Rosenblum |
| 7,471,993 B2 | 12/2008 | Rosenblum |
| 7,774,097 B2 | 8/2010 | Rosenblum |
| 7,896,243 B2 | 3/2011 | Herskovitz |
| 8,033,424 B2 | 10/2011 | Rosenblum |
| 8,095,236 B2 | 1/2012 | Rudy et al. |
| 8,191,719 B2 | 6/2012 | van Ooyen et al. |
| 8,267,310 B2 | 9/2012 | Waugh et al. |
| 8,465,243 B2 | 6/2013 | Ooyen et al. |
| 8,527,090 B2 | 9/2013 | Monto et al. |
| 8,577,145 B2 | 11/2013 | Panetta |
| 8,647,573 B2 | 2/2014 | Regan et al. |
| 8,695,814 B2 | 4/2014 | Ooyen et al. |
| 8,712,586 B2 | 4/2014 | Allinson |
| 8,738,177 B2 | 5/2014 | Ooyen et al. |
| 8,744,619 B2 | 6/2014 | Rosenblum |
| 8,789,748 B2 | 7/2014 | Waugh et al. |
| 8,849,449 B2 | 9/2014 | Waugh et al. |
| 8,862,266 B2 | 10/2014 | Van et al. |
| 9,036,894 B2 | 5/2015 | Panetta |
| 2003/0136794 A1 | 7/2003 | Chirnomas |
| 2003/0234259 A1 | 12/2003 | Selfridge et al. |
| 2004/0026441 A1 | 2/2004 | Chirnomas |
| 2004/0164146 A1 | 8/2004 | Rosenblum |
| 2004/0215369 A1 | 10/2004 | Rosenblum |
| 2005/0211720 A1 | 9/2005 | Chirnomas |
| 2005/0263536 A1 | 12/2005 | Selfridge et al. |
| 2006/0074524 A1 | 4/2006 | Chirnomas |
| 2006/0149587 A1 | 7/2006 | Hill, Sr. et al. |
| 2007/0043469 A1* | 2/2007 | Draper ............... G06F 19/3462 700/231 |
| 2007/0162184 A1* | 7/2007 | Pinney ............... G06F 19/3462 700/241 |
| 2007/0250346 A1 | 10/2007 | Luciano, Jr. et al. |
| 2007/0293982 A1 | 12/2007 | Rosenblum |
| 2008/0164279 A1 | 7/2008 | Chirnomas et al. |
| 2008/0272142 A1 | 11/2008 | Chirnomas |
| 2009/0048712 A1 | 2/2009 | Rosenblum |
| 2009/0076650 A1 | 3/2009 | Faes |
| 2010/0198401 A1 | 8/2010 | Waugh et al. |
| 2010/0232640 A1 | 9/2010 | Friend et al. |
| 2010/0268380 A1 | 10/2010 | Waugh et al. |
| 2010/0324728 A1 | 12/2010 | Rosenblum |
| 2011/0264259 A1 | 10/2011 | Boyer et al. |
| 2012/0004770 A1 | 1/2012 | Ooyen et al. |
| 2012/0012606 A1* | 1/2012 | Longley ............... G07F 11/58 221/92 |
| 2012/0089249 A1 | 4/2012 | Rosenblum |
| 2012/0232693 A1 | 9/2012 | Allinson |
| 2013/0251479 A1 | 9/2013 | Waugh et al. |
| 2013/0284755 A1* | 10/2013 | Yuyama ............... A61J 7/02 221/13 |
| 2014/0154044 A1 | 6/2014 | Ooyen et al. |
| 2015/0019008 A1 | 1/2015 | Ooyen et al. |
| 2015/0025679 A1 | 1/2015 | Rosenblum |
| 2015/0134106 A1 | 5/2015 | Boyer et al. |

\* cited by examiner

SYSTEMS AND METHODS FOR DISPENSING PRESCRIPTION MEDICATION USING A MEDICATION DISPENSING MACHINE

CROSS-REFERENCE TO RELATED APPLICATIONS

This application claims priority to U.S. Provisional Patent App. No. 61/832,151, filed on Jun. 7, 2013, and titled "Prescription Vending Machine," the entirety of which is hereby incorporated herein by reference.

BACKGROUND

Field of the Invention

The embodiments described herein are generally directed to the dispensation of prescription medication, and, more particularly, to the automatic or semi-automatic dispensation of prescription medication using a vending-type medication-dispensing machine.

Description of the Related Art

In order to better serve low-income patients, the 340B Drug Pricing Program was made part of the Public Health Service Act, codified as 42 U.S.C. §256b, in 1992. Under the 340B Drug Pricing Program, drug manufacturers are required to provide outpatient drugs to eligible healthcare organizations and covered entities at significantly reduced prices. The primary goal of the program is to help provide quality healthcare to low-income populations in the form of access to medications that might otherwise be unaffordable. In furtherance of this goal, one of the objectives of the program is to have 100% accountability for both the medications and patient eligibility.

In the past, paper-based prescription systems and extensive networks of pharmacies have made it difficult to ensure accountability. However, in the last several years, the widespread adoption of electronic prescriptions has enabled much better tracking and accountability. Today, approximately 85% of prescriptions are filed electronically. In addition to enabling better tracking of and accountability for medication distribution, electronic prescriptions have also allowed for the accumulation of better and more comprehensive patient data.

For example, data from 2010-2012 demonstrates that approximately 30% of prescriptions are never filled. Thus, 30% of patients visited the doctor and received a prescription, but never picked up the prescription. In addition, 45% of patients who did pick up their prescriptions were no longer following those prescriptions within six months. In other words, these patients failed to pick up refills for their prescriptions.

"Medication non-adherence" refers to instances in which patients do not follow their physicians' prescriptions. Some of the leading causes of medication non-adherence are the time, effort, and inconvenience of visiting a pharmacy to pick up prescribed medications. In fact, the average wait time at a pharmacy is forty-five minutes. Given the inconvenience and inefficiency of the current system, it is not surprising that 30% of prescriptions are never filled.

Side effects of medication non-adherence include hospital readmissions. Specifically, when a patient does not follow his or her doctor's orders to take a particular medication, the end result is often another trip to the hospital or doctor's office. Under the Affordable Care Act of 2010, hospitals are now subject to monetary penalties for readmissions in the form of reductions in Medicare reimbursements. Therefore, hospitals now have even more of an incentive to ensure that patients get quality care and follow the instructions they are given, in order to reduce the number of readmissions.

One way to encourage patients to fill and follow their prescriptions is to make it easy and convenient for them to fill those prescriptions. A vending-type, medication-dispensing machine is one means for streamlining the process for prescription fulfillment. For instance, when the Marin County Clinic in California became aware of the extremely high rate of medication non-adherence for electronic prescriptions, the clinic installed a machine-based medication-dispensing system. As a result, the clinic saw its medication non-adherence rate drop from 30% down to 3.4% in the course of one year. One likely reason for this increase in adherence is that the average time to fill a prescription is now a mere four minutes.

However, the machine-based medication-dispensing system at the Marin County Clinic still requires a licensed pharmacist to be physically present. This is because the California State Board of Pharmacies requires either a licensed pharmacist or a technician under the "direct supervision" of a licensed pharmacist to oversee the "act of dispensing." The "act of dispensing" is defined as taking the drug off the shelf and affixing the label to it. However, after the drug has been properly identified and labeled, any person can hand it to the patient.

A large clinic, such as the Marin County Clinic, can afford to have a pharmacist physically present at all times. Thus, in such a large clinic, it is not difficult to comply with the rules that govern the dispensation of medications. However, at smaller clinics, pharmacies, or other dispensaries, there may not be enough volume of business to support the presence of a full-time pharmacist.

In order to solve this deficiency in the art, a process is needed which can use a machine to perform the act of dispensing in a manner that satisfies the rules governing the act of dispensing without necessarily requiring the physical presence of a pharmacist. Such a process could reduce the incidence of medication non-adherence, reduce readmissions, and provide better service and care to patients. In addition, the combination of such a process with electronic prescriptions may allow for 100% accountability for the dispensation of medications, including patient identification, as well as documentation that the patient received the prescribed medication. Such accountability is advantageous for Medicare reimbursement and for compliance with the 340B Drug Pricing Program.

SUMMARY

Accordingly, systems and methods are disclosed for dispending prescription medication using a medication-dispensing machine.

In an embodiment, a method for dispensing prescription medication is disclosed. The method comprises using at least one hardware processor of a medication-dispensing machine to: receive an identification of medication and patient information for an electronic prescription; retrieve a container of the identified medication from a plurality of containers of medication that are stocked within the medication-dispensing machine, wherein each of the plurality of containers of medication comprises a first barcode; scan the first barcode of the retrieved container; generate a patient label based on at least the patient information; apply the patient label to the retrieved container; capture an image of the retrieved container; provide the captured image over at least one network to a pharmacist; receive approval over the at least one network from the pharmacist; and, based on the approval, release the retrieved container to a user.

In a further embodiment, the applied patient label comprises a second barcode, and the method further comprises using the at least one hardware processor to, prior to releasing the retrieved container to the user, scan the first barcode on the retrieved container and the second barcode on the applied patient label; and confirm that data encoded in the first barcode corresponds to data encoded in the second barcode.

In a further embodiment, the medication-dispensing machine comprises a display, and the method further comprises using the at least one hardware processor to establish real-time communication, over the at least one network, between the user and the pharmacist via the display.

In a further embodiment, the medication-dispensing machine comprises a dispensing enclosure with a door that can be switched between a locked state and an unlocked state, and the method further comprises using the at least one hardware processor to place the retrieved container within the dispensing enclosure while the door is in a locked state, and wherein releasing the retrieved container to the user comprises switching the door to an unlocked state.

In a further embodiment, the method comprises using the at least one hardware processor to receive a signature from the user, and releasing the retrieved container to the user is further based on receiving the signature from the user.

In a further embodiment, the method comprises using the at least one hardware processor to receive a payment for the identified medication from the user, wherein releasing the retrieved container to the user is further based on the payment.

In a further embodiment, the plurality of containers of medication comprise a plurality of subsets of one or more containers of medication, and each of the plurality of subsets comprises a container having a different size or shape than other ones of the plurality of subsets.

In a further embodiment, retrieving the container of the identified medication comprises controlling a mechanical arm, comprising one or more joints and a claw, to grab the container of the identified medication from a platform within the medication dispensing machine, wherein the platform supports a plurality of containers of medication.

In a further embodiment, the method comprises using the at least one hardware processor to receive an identification of the user from the user, and retrieving the container of the identified medication is performed after receiving the identification of the user.

In a further embodiment, the captured image comprises one of a photograph and a video.

In an additional embodiment, a medication-dispensing machine is disclosed. The medication-dispensing machine comprises: at least one hardware processor; a mechanical device for retrieving a container of medication from a plurality of containers of medication that are stocked within the medication-dispensing machine, wherein each of the plurality of containers of medication comprise a first barcode; a dispensing enclosure comprising a door which can be switched between a locked state and an unlocked state; and one or more executable modules that, when executed by the at least one hardware processor, receive an identification of medication and patient information for an electronic prescription, control the mechanical device to retrieve a container of the identified medication from the plurality of containers of medication and place the retrieved container within the dispensing enclosure while the door is in the locked state, control a barcode scanner to scan the first barcode of the retrieved container, generate a patient label based on at least the patient information, apply the patient label to the retrieved container, control a camera to capture an image of the retrieved container, provide the captured image over at least one network to a pharmacist, receive approval over the at least one network from the pharmacist, and, based on the approval, release the retrieved container to a user by at least switching the door of the dispensing enclosure to the unlocked state.

In a further embodiment, the applied patient label comprises a second barcode, and the one or more executable modules are configured to, prior to releasing the retrieved container to the user: control the barcode scanner to scan the first barcode on the retrieved container and the second barcode on the applied patient label; and confirm that data encoded in the first barcode corresponds to data encoded in the second barcode.

In a further embodiment, the machine comprises a display, and the one or more executable modules are configured to establish real-time communication, over the at least one network, between the user and the pharmacist via the display. The real-time communication may comprise audio and video.

In a further embodiment, the machine comprises a touch panel, and the one or more executable modules are configured to receive a signature from the user via the touch panel, and releasing the retrieved container to the user is further based on receiving the signature from the user.

In a further embodiment, the one or more executable modules are configured to receive a payment for the identified medication from the user, and releasing the retrieved container to the user is further based on the payment.

In a further embodiment, the plurality of containers of medication comprise a plurality of subsets of one or more containers of medication, and each of the plurality of subsets comprises a container having a different size or shape than other ones of the plurality of subsets.

In a further embodiment, the machine comprises one or more platforms, each of the one or more platforms supports a plurality of containers of medication, the mechanical device comprises a mechanical arm comprising one or more joints and a claw, and controlling the mechanical device to retrieve a container of the identified medication comprises controlling the mechanical arm to grab the container of the identified medication from one of the one or more platforms.

In a further embodiment, the one or more executable modules are configured to receive an identification of the user from the user, and control the mechanical device to retrieve the container of the identified medication after receiving the identification of the user.

In a further embodiment, the captured image comprises one of a photograph and a video.

BRIEF DESCRIPTION OF THE DRAWINGS

The details of the present invention, both as to its structure and operation, may be gleaned in part by study of the accompanying figures, in which like reference numerals refer to like parts, and in which.

DETAILED DESCRIPTION

Figure 1:
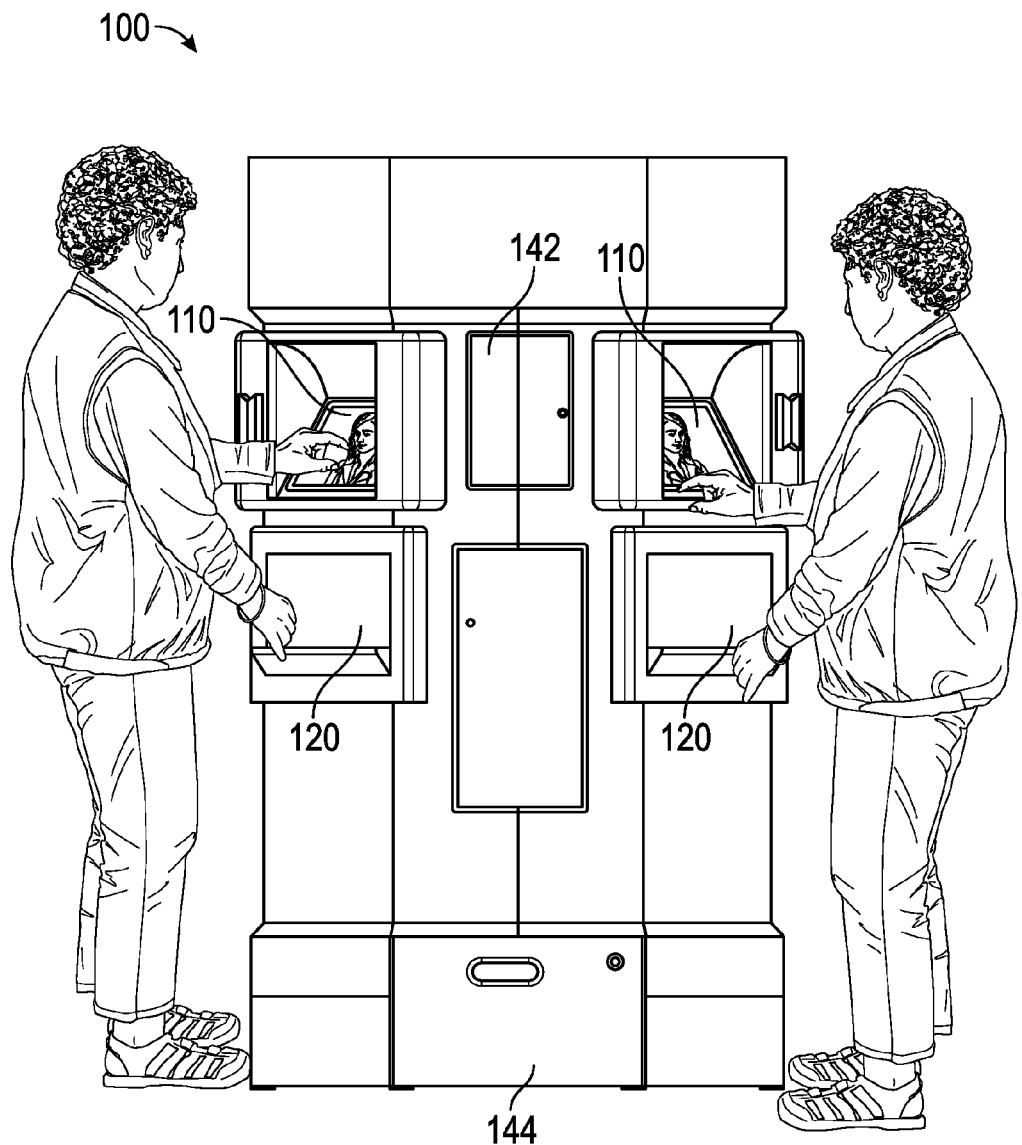
FIG. 1 illustrates a front external view of a medication-dispensing machine, according to an embodiment.

After reading this description, it will become apparent to one skilled in the art how to implement the invention in various alternative embodiments and alternative applications. However, although various embodiments of the present invention will be described herein, it should be understood that these embodiments are presented by way of example and illustration only, and not limitation. As such, this detailed description of various embodiments should not be construed to limit the scope or breadth of the present invention as set forth in the appended claims.

In an embodiment, systems and methods are disclosed for the dispensation of prescription medication using a machine, such as a prescription vending machine. Specifically, a pharmaceutical vending machine may be configured to dispense medications under the remote supervision of a licensed pharmacist.

One benefit that may result from use of the disclosed embodiments is vastly improved safety. For example, in an embodiment, the prescription vending machine or "medication-dispensing machine" scans the barcode of each selected container of medication both before and after it is labeled with a patient label. Mismatching of labels can be prevented by the post-labeling scan which scans a barcode of the container of medication and a barcode on the patient label to ensure a match between the two.

In addition, in an embodiment, a labeled container of medication may be subjected to a visual inspection by a pharmacist prior to being released to a patient. This is an improvement over the typical situation in a pharmacy in which multiple labels are often sent to a common printer, and then picked up and applied by a technician. Such a situation allows for the possibility of a mismatch of a patient label to a container of medication, due to human error.

Furthermore, safety may be further improved because, in an embodiment, the inventory stocked in the medication-dispensing machine comprises individual units of use, rather than bulk packages of pills. Some conventional dispensing machines stock large bottles of bulk pills, and count out the necessary amount for each order. However, in these conventional machines, all of the pills travel down the same chute to get to individual prescription containers, which can result in contamination of the pills. For example, if the chute becomes contaminated with penicillin dust, a subsequent batch of pills that travels down the chute may become contaminated with the penicillin dust. The result of this contamination could be dire if the patient receiving the contaminated batch of pills has a penicillin allergy. By providing a medication-dispensing machine that dispenses individual units of use (e.g., in their individual packaging materials, as provided by the manufacturer), this type of cross-contamination can be avoided.

Advantageously, in embodiments which stock individual units of use, any medication on the market can be dispensed using the disclosed systems and methods. Conventional systems are limited to handling only one size and shape of bottle, which severely curtails their usefulness and compatibility. In embodiments of the disclosed systems and methods, the medication-dispensing machine may be configured to manage containers of medication of all shapes and sizes, including bottles, boxes, tubes, and the like. Such a configuration allows any medication to be stocked and dispensed.

As will be discussed below, the medication-dispensing machine can make the overall medication-dispensing process more efficient, since, in embodiments, a pharmacist does not have to be physically present to approve the dispensation of medication, and can release medication to a patient remotely. In addition, one pharmacist may cover multiple machines, which may all be within one dispensary or distributed across multiple geographical locations (e.g., multiple dispensaries). The pharmacist is freed from the legwork of selecting and labeling medications, and therefore, can focus instead on safety concerns, such as drug identification and interactions, as well as patient care, such as consulting with patients and answering the patients' questions. With one pharmacist able to cover multiple dispensing machines, pharmaceutical operations, which utilize the machines and processes described herein, become more affordable for clinics, hospitals, doctors' offices, and other dispensaries.

The medication-dispensing machines may come in various sizes and shapes and contain various sizes and shapes of inventories. In addition, the medication-dispensing machines may contain specialized inventory, depending on their locations. For example, a machine located in a cardiology department of a hospital could primarily contain cardiac medications. Having machines placed conveniently in multiple locations can increase patient convenience, thereby reducing instances of medication non-adherence.

Example Medication-Dispensing Machine

In an embodiment, a medication-dispensing machine or "vending" machine is utilized in the prescription-dispensing process disclosed herein. The machine may be capable of selecting the correct medication for a patient from a plurality of stocked medications, applying a label to the selected medication, and enabling a remotely-located pharmacist to consult with the patient and/or verify and release the medication to the patient. Thus, the pharmacist may retain control of the whole medication-dispensing process, regardless of whether or not the pharmacist is physically present in a vicinity of the machine.

FIGS. 1-17 illustrate a medication-dispensing machine 100, according to embodiments. However, it should be understood that different embodiments, designs, and configurations may be utilized for such a machine, as long as the machine is capable of performing one or more of the functions described in embodiments of the prescription-dispensing process disclosed herein.

Figure 2:
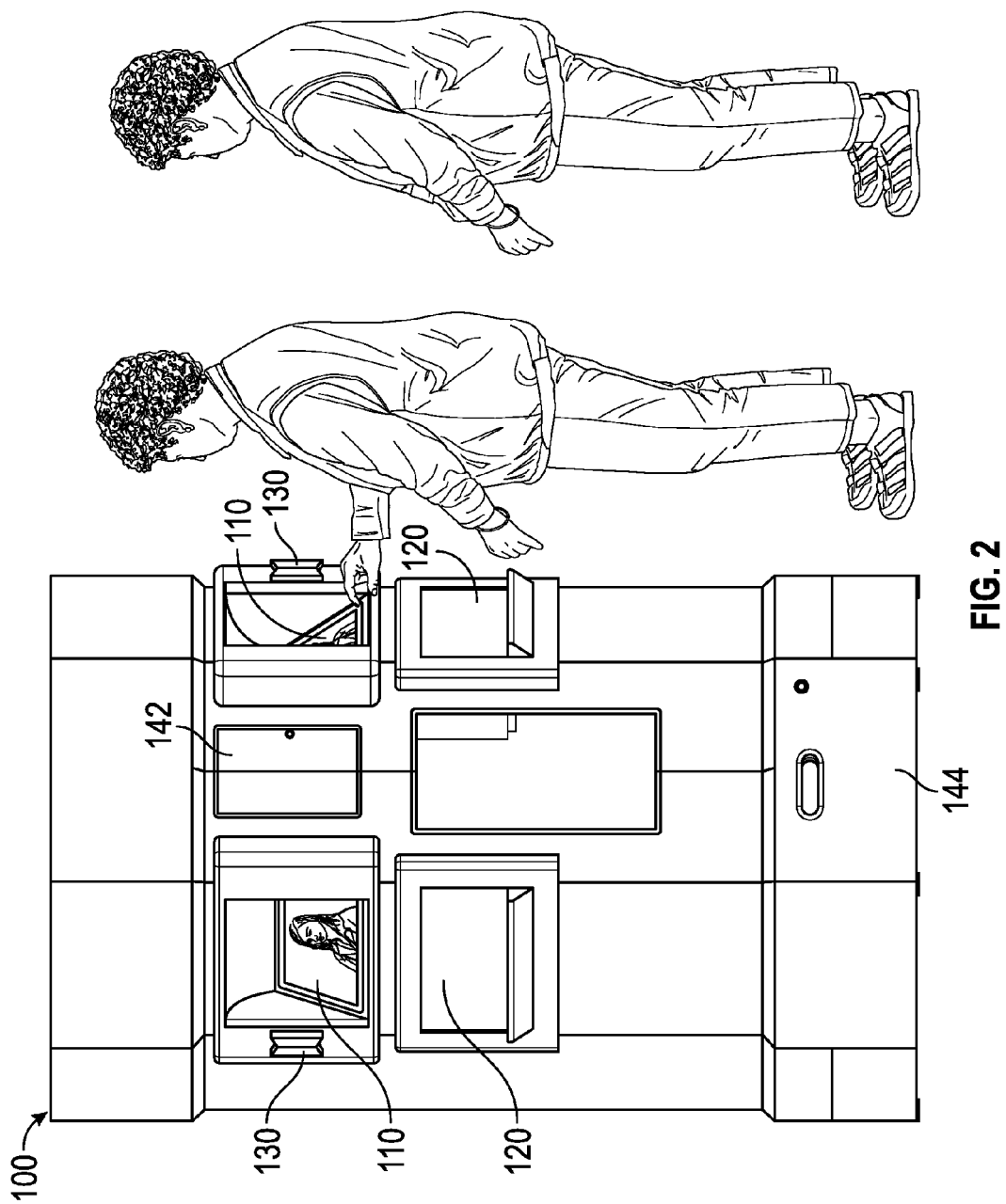
FIG. 2 illustrates a front angled view of a medication-dispensing machine, according to an embodiment.

FIGS. 1 and 2 are external views of a medication-dispensing machine 100, according to an embodiment. In the illustrated embodiment, machine 100 comprises two human-to-machine interfaces. However, it should be understood that machine 100 may comprise any feasible number of human-to-machine interfaces, including one human-to-machine interface or three or more human-to-machine interfaces.

Figure 3:
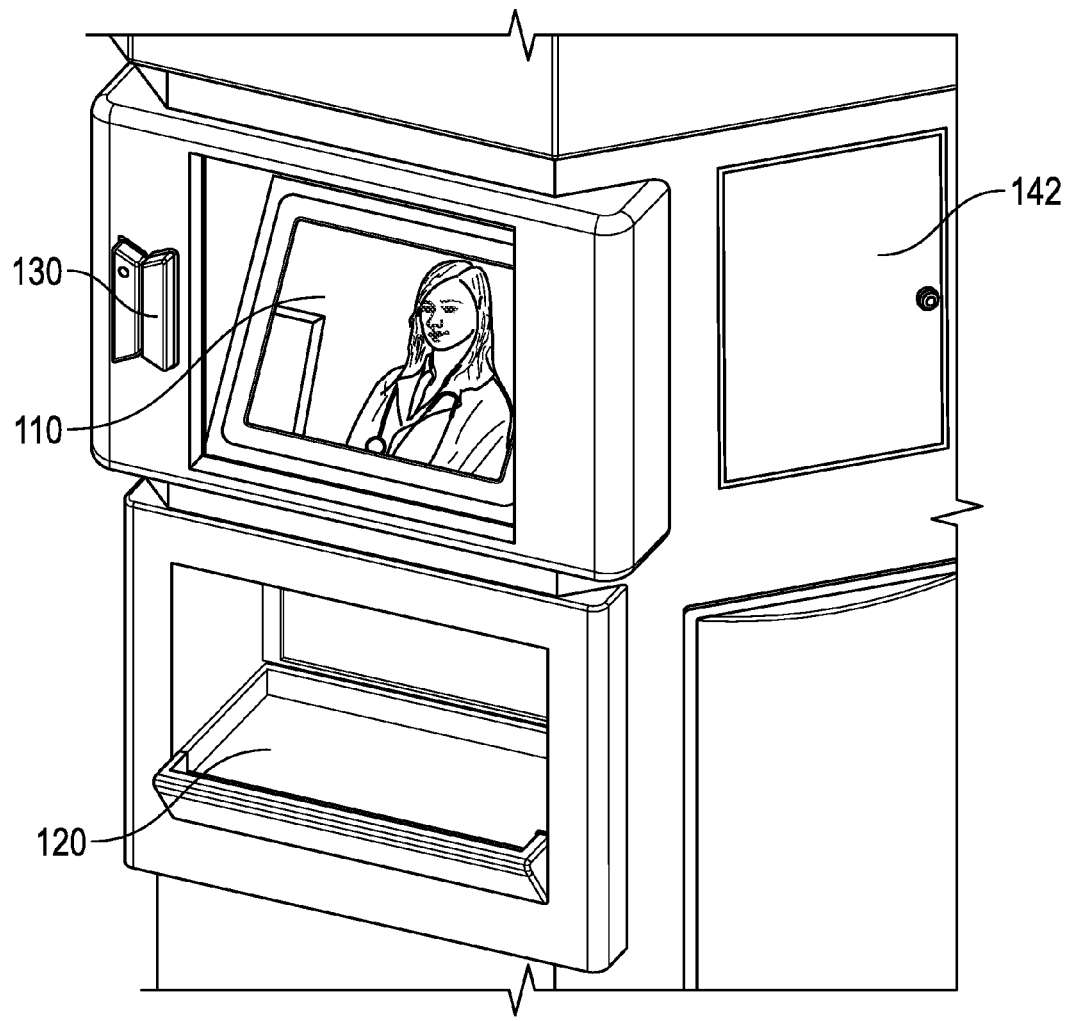
FIG. 3 illustrates a human-to-machine interface of a medication-dispensing machine, according to an embodiment.

FIG. 3 is a closer view of a human-to-machine interface from FIGS. 1 and 2, according to an embodiment. As depicted, each human-to-machine interface may comprise a display 110 and a dispensing enclosure 120, into which machine 100 may place a medication to be dispensed, and which can be opened and/or unlocked such that a user can grab the medication, as well as closed and/or locked to prevent a user from grabbing the medication or otherwise reaching inside of machine 100 (e.g., prior to a medication being released to the patient). In addition, display 110 of the human-to-machine interface may comprise a touch panel, which allows a user to input data to, or select data from, display 110. Alternatively or additionally, the human-to-machine interface may be provided with other inputs, such as buttons, a keyboard or keypad, a pointing device such as a mouse or trackball, etc. (none of which are shown). Furthermore, as illustrated, the human-to-machine interface may comprise a separate payment or card-reading input 130, such as a credit card reader and/or insurance or benefit-plan card reader, to collect payment and/or insurance/benefit-plan information from the user. The human-to-machine interface may also comprise other elements, not mentioned or shown. For example, the human-to-machine interface may comprise microphone(s) which collect speech or other audio from a user and/or speaker(s) which produce speech or other audio to the user.

Figure 4:
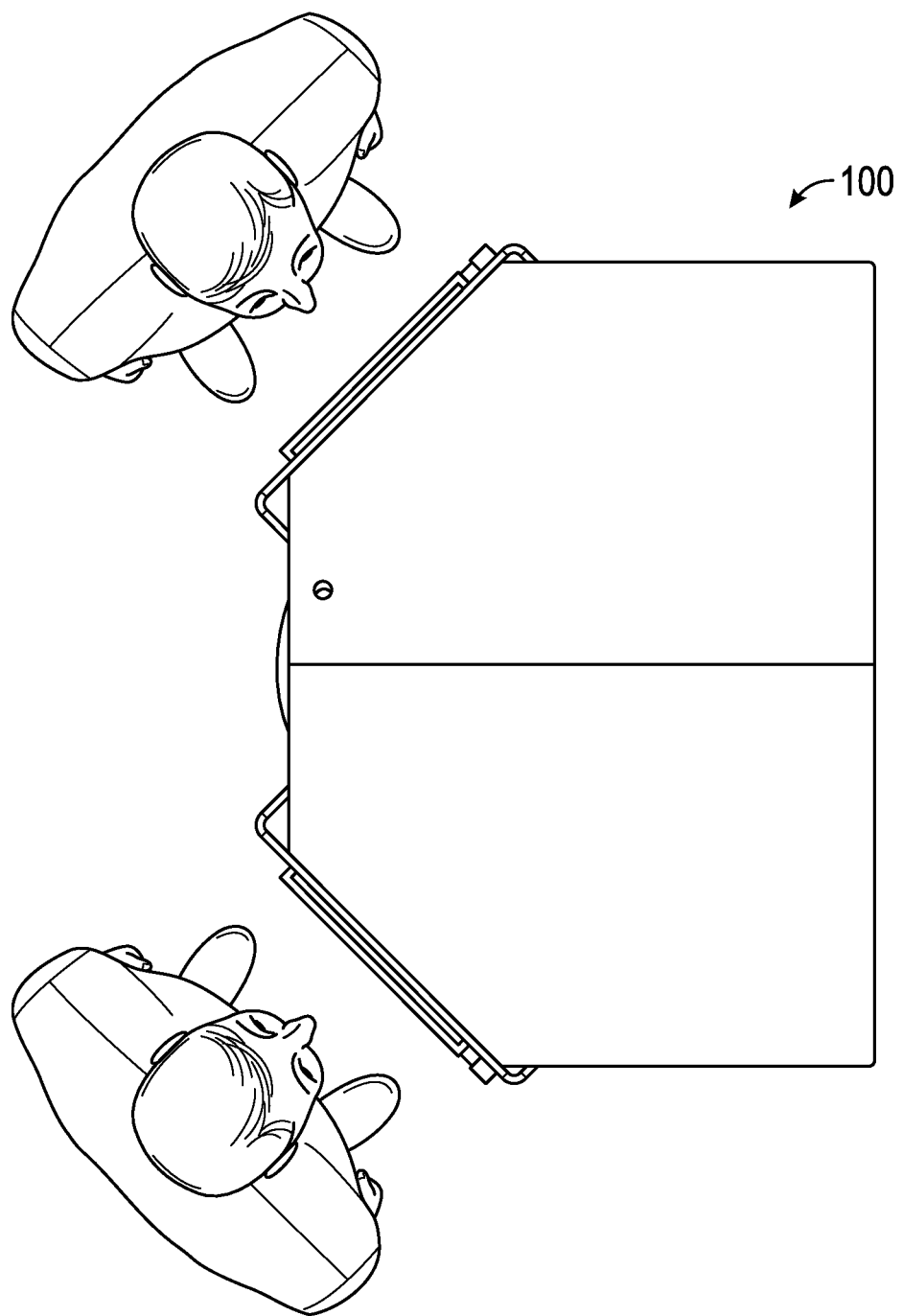
FIG. 4 illustrates an overhead view of a medication-dispensing machine, according to an embodiment.

As depicted in FIGS. 1 and 2, in embodiments of medication-dispensing machine 100 which are configured with multiple human-to-machine interfaces, the human-to-machine interfaces may be angled with respect to each other, as shown in FIG. 4, and/or the displays 110 inset such that a user can only view one display 110 at a time and/or only one user can view a display 110 at a time. Such features mitigate the risk that a user's privacy may be compromised, for example, by another individual viewing personal information displayed on display 110 of the human-to-machine interface with which the user is interacting.

As depicted in FIGS. 1 and 2, medication-dispensing machine 100 may also comprise one or more access panels 142 and 144 which provide access to the internal components of the machine. For example, access may be provided to an internal chamber of machine 100, which houses the stocked medication, to allow an administrator (e.g., pharmacist, technician, etc.) to restock machine 100 with medication. Access may also be provided to various internal components of machine 100 to enable machine 100 to be serviced, repaired, upgraded, etc. For example, access may be provided via panels 142 and/or 144 to any of the various components of internal structure 200, described below, including electronic processing device(s) of machine 100.

Figure 5:
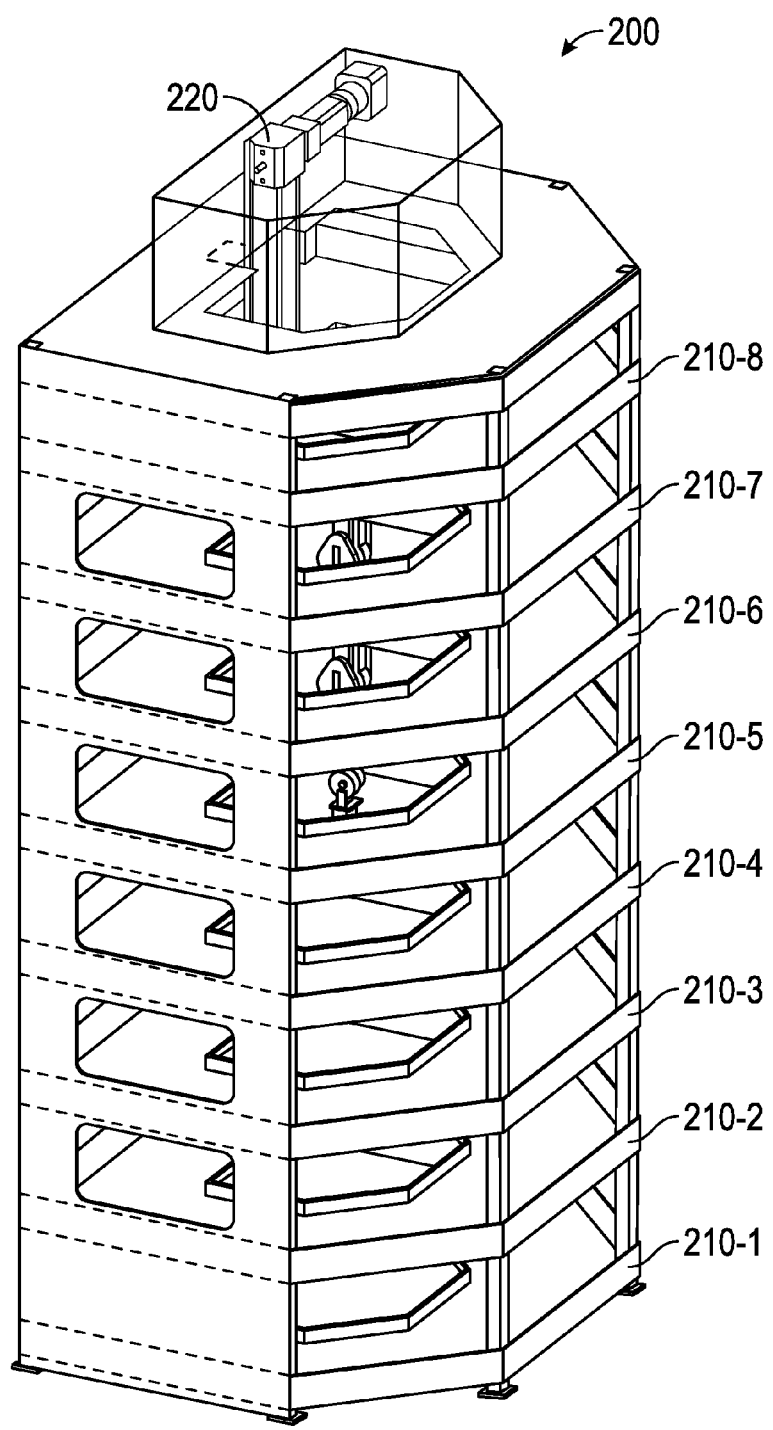
FIG. 5 illustrates a front angled view of the internal structure of a medication-dispensing machine, according to an embodiment.

FIG. 5 illustrates an internal structure 200 of medication-dispensing machine 100 depicted in FIGS. 1-4, according to an embodiment. As illustrated, internal structure 200 of machine 100 comprises one or more shelves or platforms 210. While internal structure 200 is illustrated as having eight platforms 210 (i.e., 210-1 through 210-8), it should be understood that internal structure 200 may have any number of platforms 210, including one or any plurality of platforms 210. Each platform 210 is configured to support a plurality of medications with which the machine 100 has been stocked, and has an opening in the center. Each platform may be accessible from outside machine 100—for example, via one or more access panels, such as access panels 142 and/or 144—such that machine 100 can be restocked with medication as needed. Alternatively or additionally, machine 100 may comprise one or more restocking drawers (e.g., in the front or back, at the top or bottom, etc.), each comprising one or more of platforms 210. In this manner, platforms 210 may be pulled out from machine 100 and restocked as needed.

Figure 6:
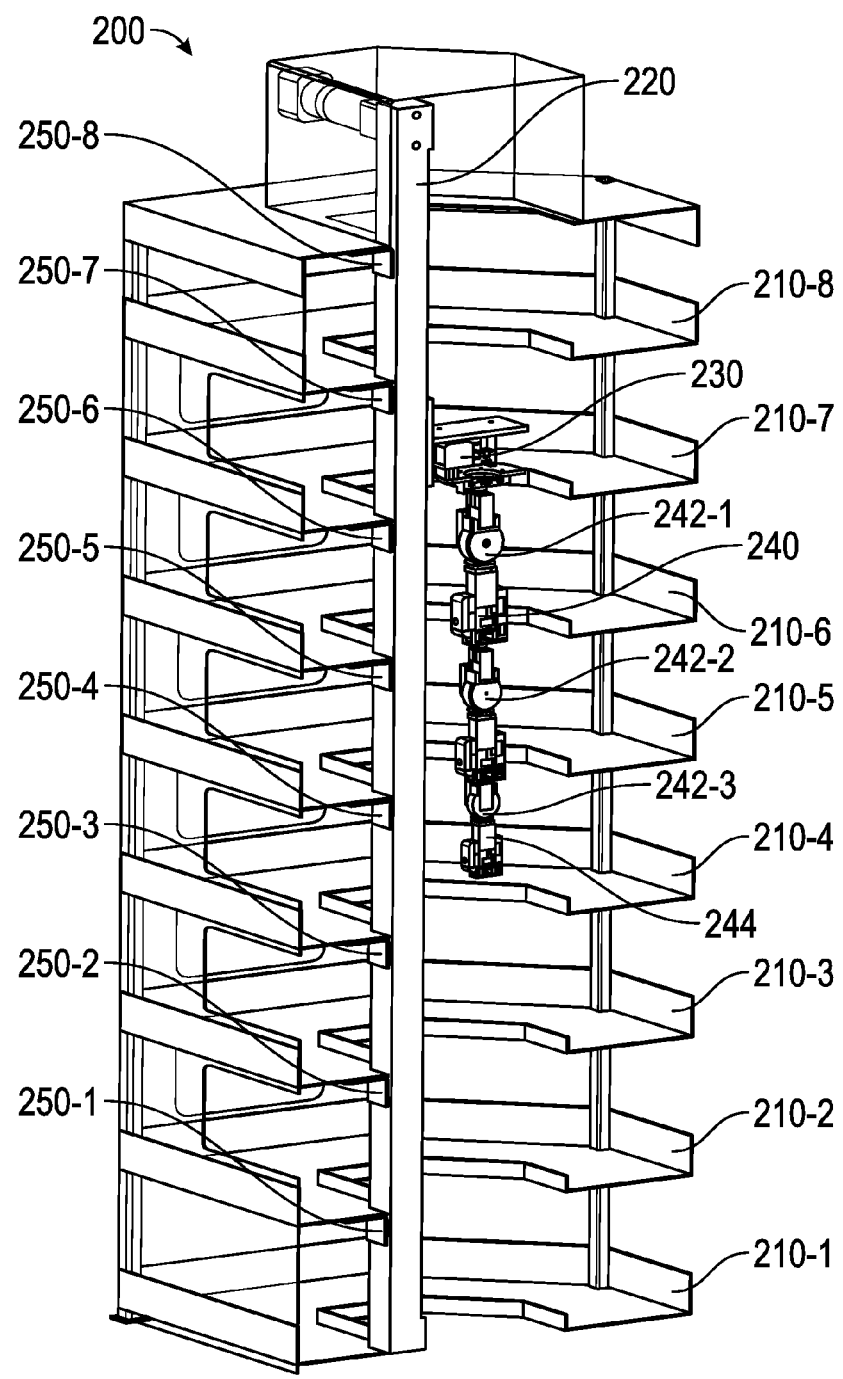
FIG. 6 illustrates a rear angled cut-away view of the internal structure of a medication-dispensing machine, according to an embodiment.

In an embodiment, internal structure 200 of medication-dispensing machine 100 also comprises a shaft 220 which runs vertically through a central portion of machine 100 by passing through the central openings of each of medication-bearing platforms 210. Shaft 220 may also be fixed to a portion of one or more, including all, of platforms 210, for example, at a side of the central openings of the platforms 210, as well as to upper and/or lower portions of machine 100. For example, as shown in FIG. 6, which is a cut-away view of internal structure 200 of medication-dispensing machine 100 depicted in FIG. 5, brackets 250 may fix portions of shaft 220 to corresponding portions of each platform 210 at fixed intervals along the length of shaft 220.

In an embodiment, medication-dispensing machine 100 also comprises a sliding connection element 230, which slidably connects shaft 220 to a mechanical arm 240. Specifically, connection element 230 may be held in a groove of shaft 220 such that it can slide vertically up and down shaft 220. Mechanical arm 240 is connected to connection element 230, such that mechanical arm 240 also slides in a vertical up or down direction in conjunction with connection element 230.

In an embodiment, mechanical arm 240 comprises one or more joints 242 and a claw 244. Joints 242 divide arm 240 into multiple segments which may be articulated at various angles with respect to each other. Accordingly, arm 240 may be controlled to take a variety of forms in order to configure claw 244 to a position and angle at which it can grab a medication container on a platform 210. In addition, since arm 240 can be moved vertically, arm 240 can be controlled and configured to grab a medication container from any one of platforms 210-1 through 210-8. Notably, shaft 220 extends higher than the highest platform (i.e., platform 210-8 in the illustrated embodiment) such that claw 244 can be appropriately positioned to reach medication containers on the highest platform. While arm 240 is illustrated with only a few joints 242, it should be understood that arm 240 may comprise any suitable number of joints 242.

Furthermore, it should be understood that internal structure 200 represents only a single possible configuration of shaft 220 with respect to platforms 210. In alternative embodiments, shaft 220 may be positioned in any position with respect to platforms 210 as long as slidable mechanical arm 240 is able to reach containers of medication stocked on platforms 210. For example, shaft 220 may be positioned on or near the outside edges of platforms 210, instead of within central openings of platforms 210, in which case there may be no need for the central openings in platforms 210.

In an embodiment, medication-dispensing machine 100 also has internal vision capabilities that allow it to identify the dimensions (e.g., size and/or shape) of a container of medication. Such internal vision may be provided in the form of one or more sensors (e.g., camera or other optical sensor, proximity sensor, etc.) on the mechanical arm 240 (e.g., on claw 244) or other component of machine 100. This vision capability allows mechanical arm 240 to pick up a package or other container of any size or shape from platform 210.

Figure 7:
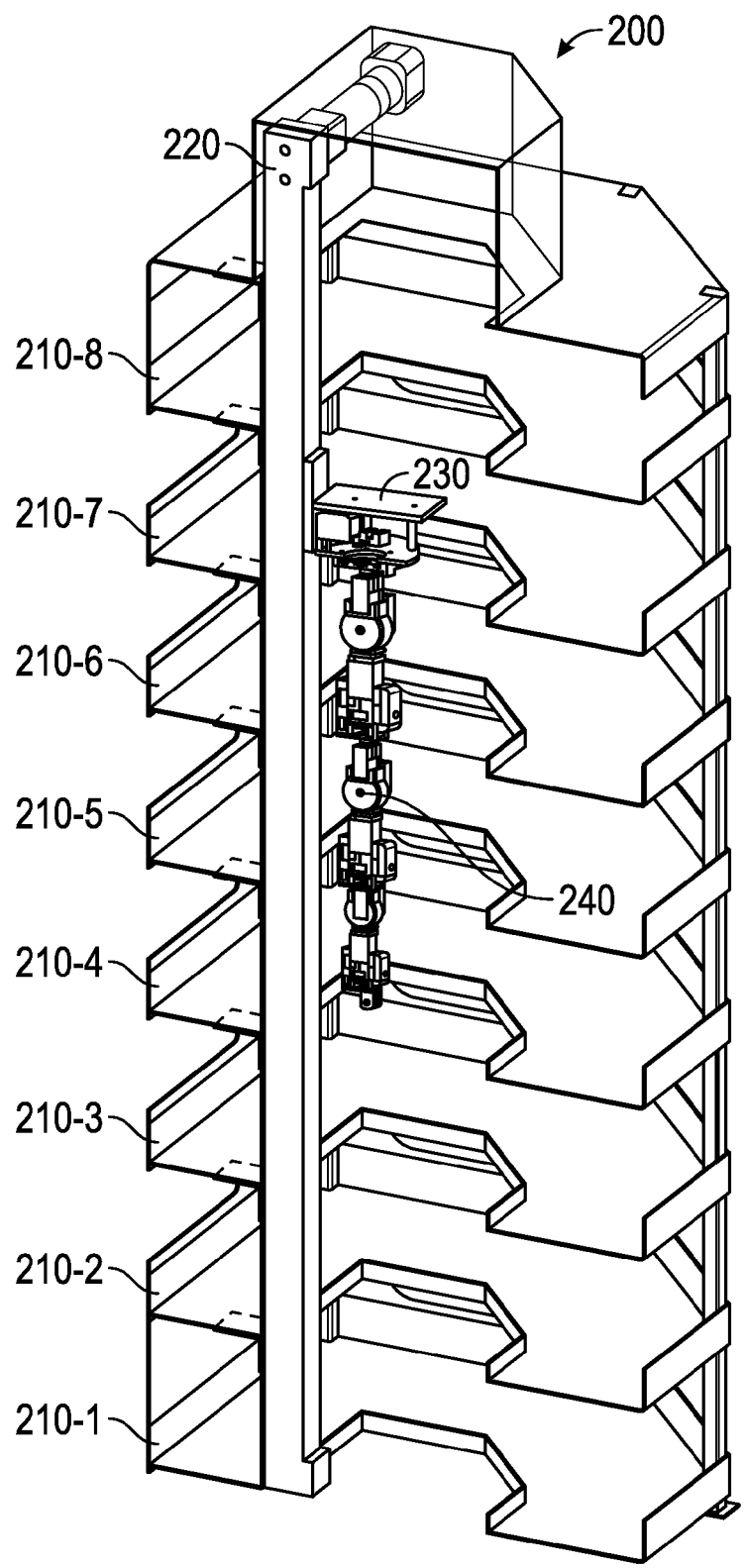
FIG. 7 illustrates a front angled cut-away view of the internal structure of a medication-dispensing machine, according to an embodiment.
Figure 8:
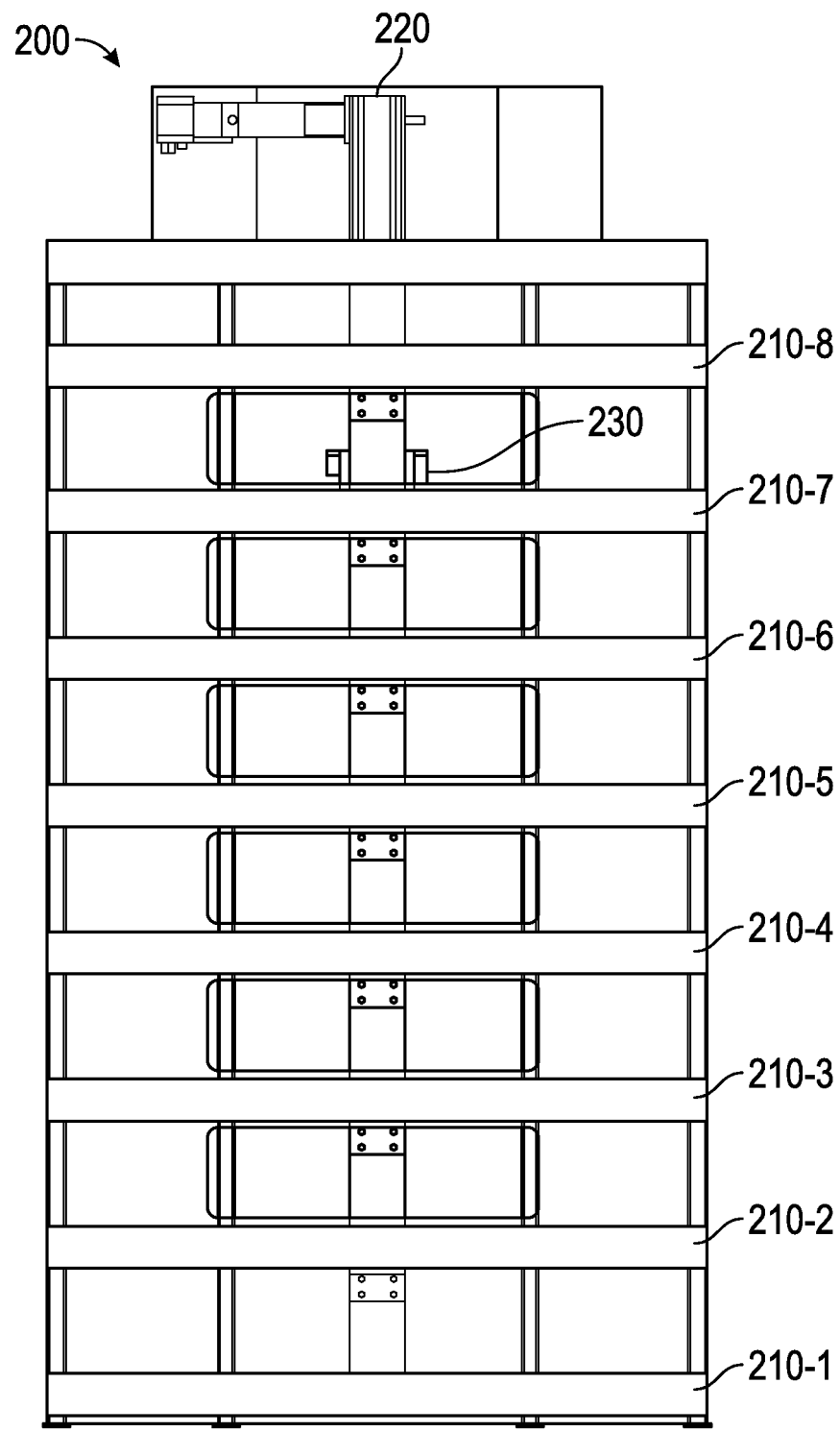
FIG. 8 illustrates a front view of the internal structure of a medication-dispensing machine, according to an embodiment.
Figure 9:
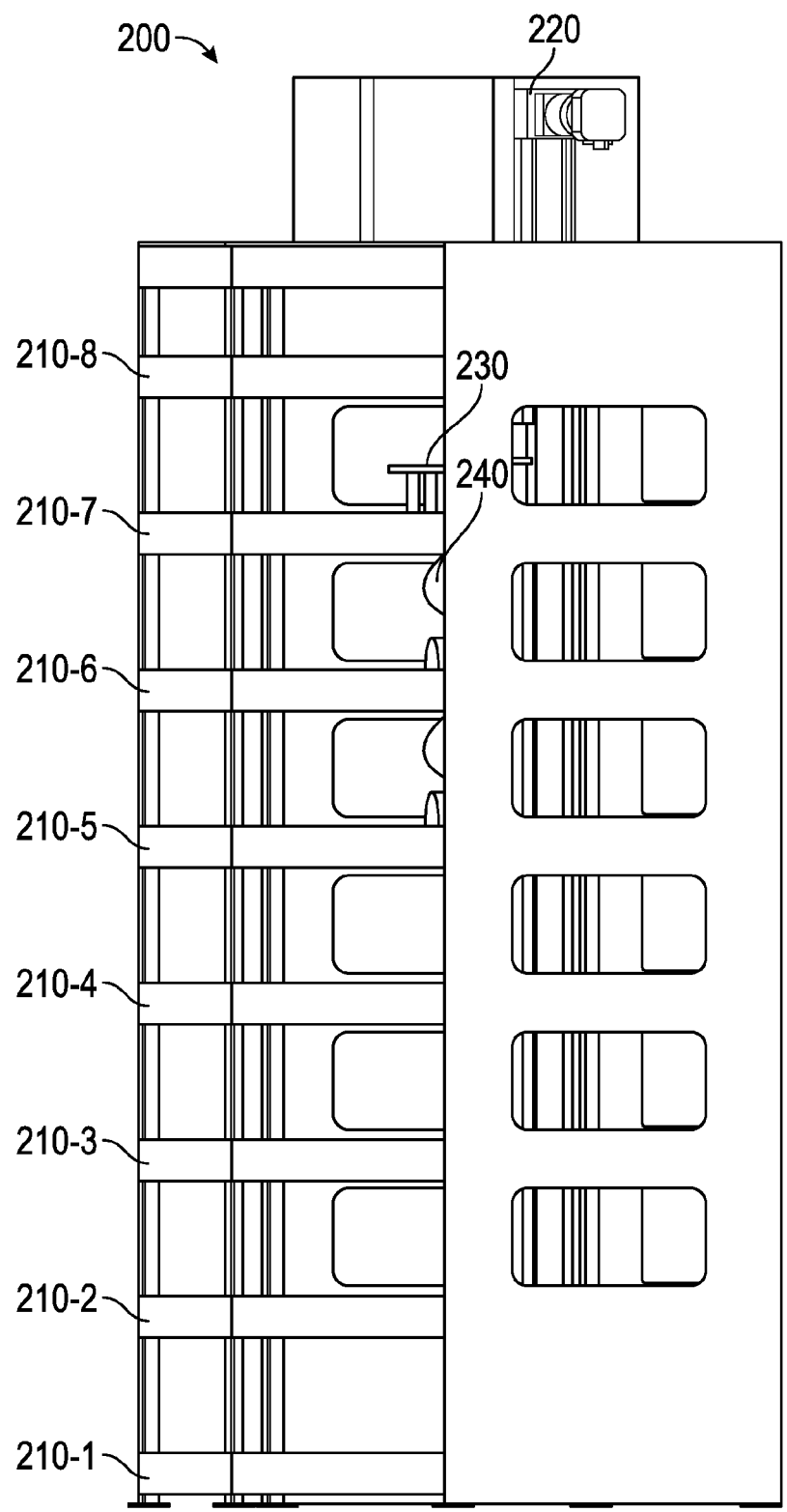
FIG. 9 illustrates a side view of the internal structure of a medication-dispensing machine, according to an embodiment.
Figure 10:
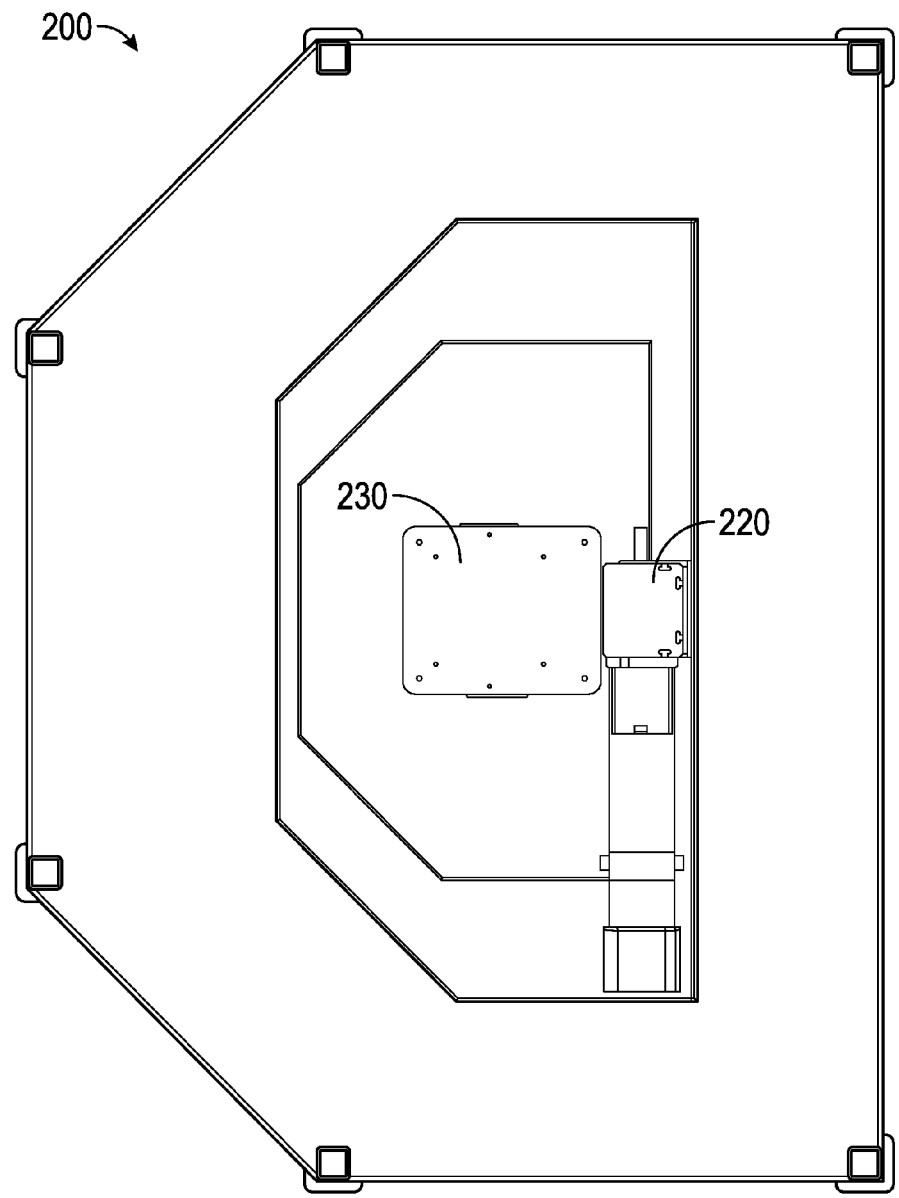
FIG. 10 illustrates an overhead view of the internal structure of a medication-dispensing machine, according to an embodiment.
Figure 11:
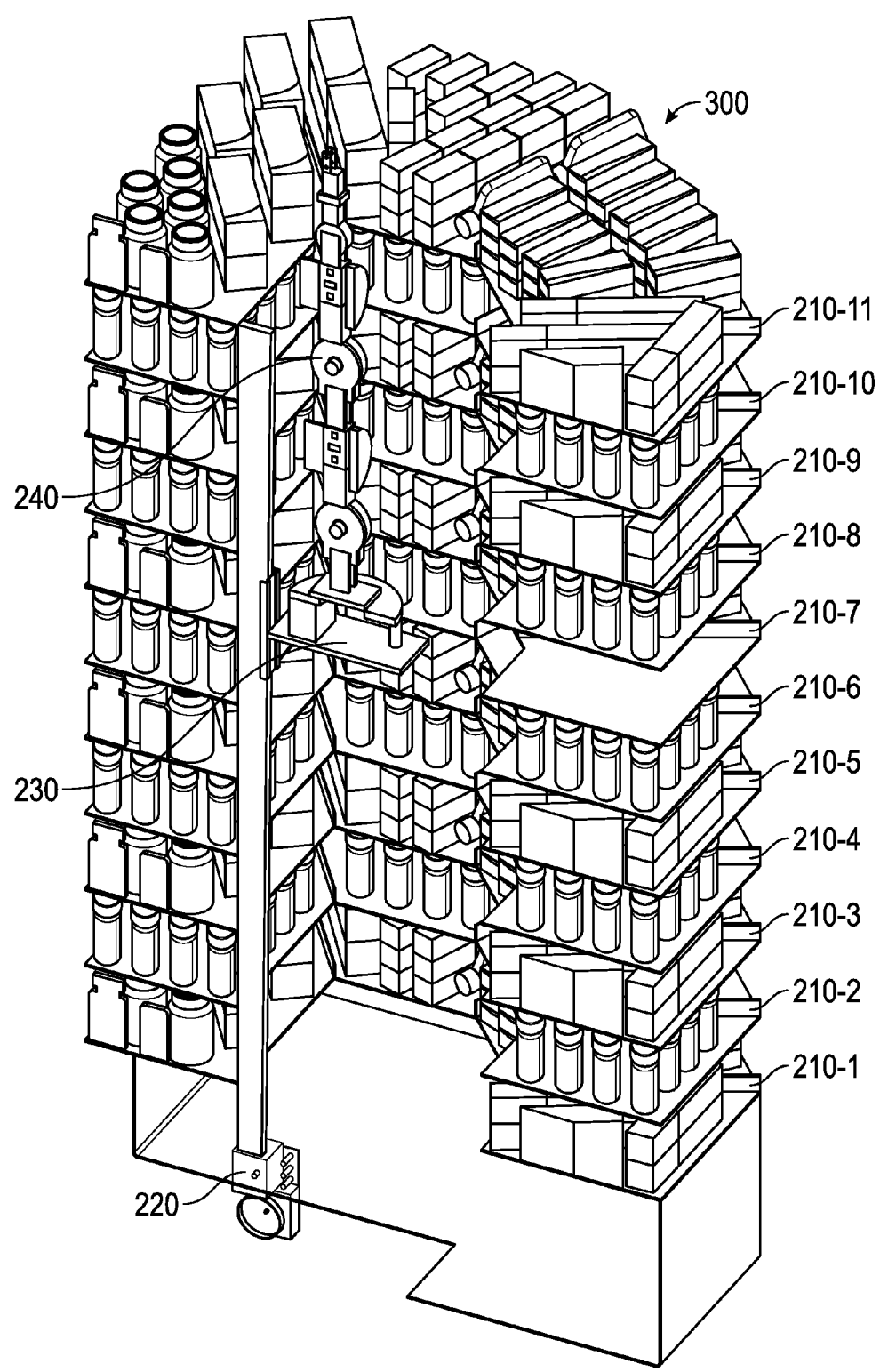
FIG. 11 illustrates a front angled cut-away view of the internal structure of a stocked medication-dispensing machine, according to an embodiment.
Figure 12:
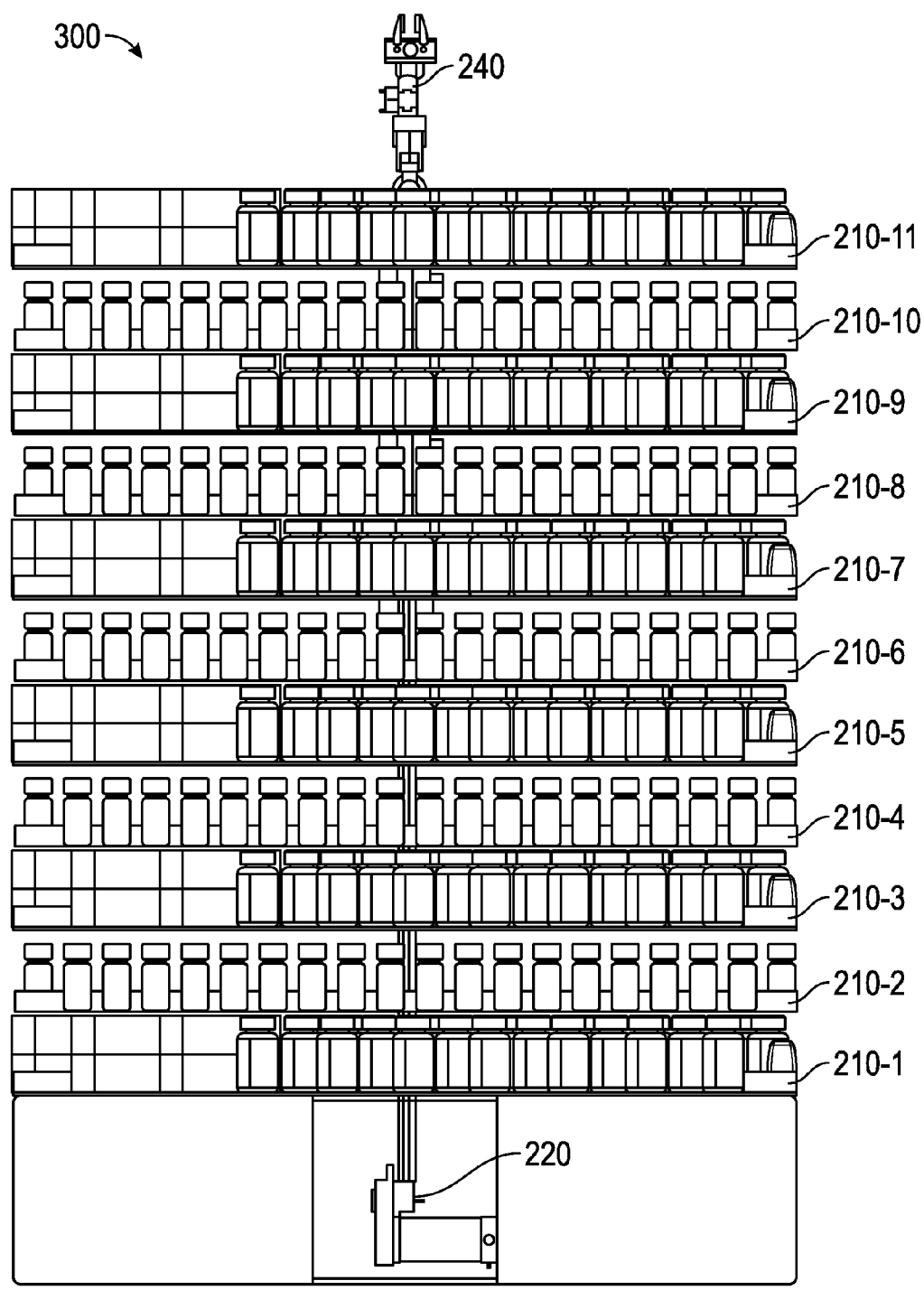
FIG. 12 illustrates a front view of the internal structure of a stocked medication-dispensing machine, according to an embodiment.
Figure 13:
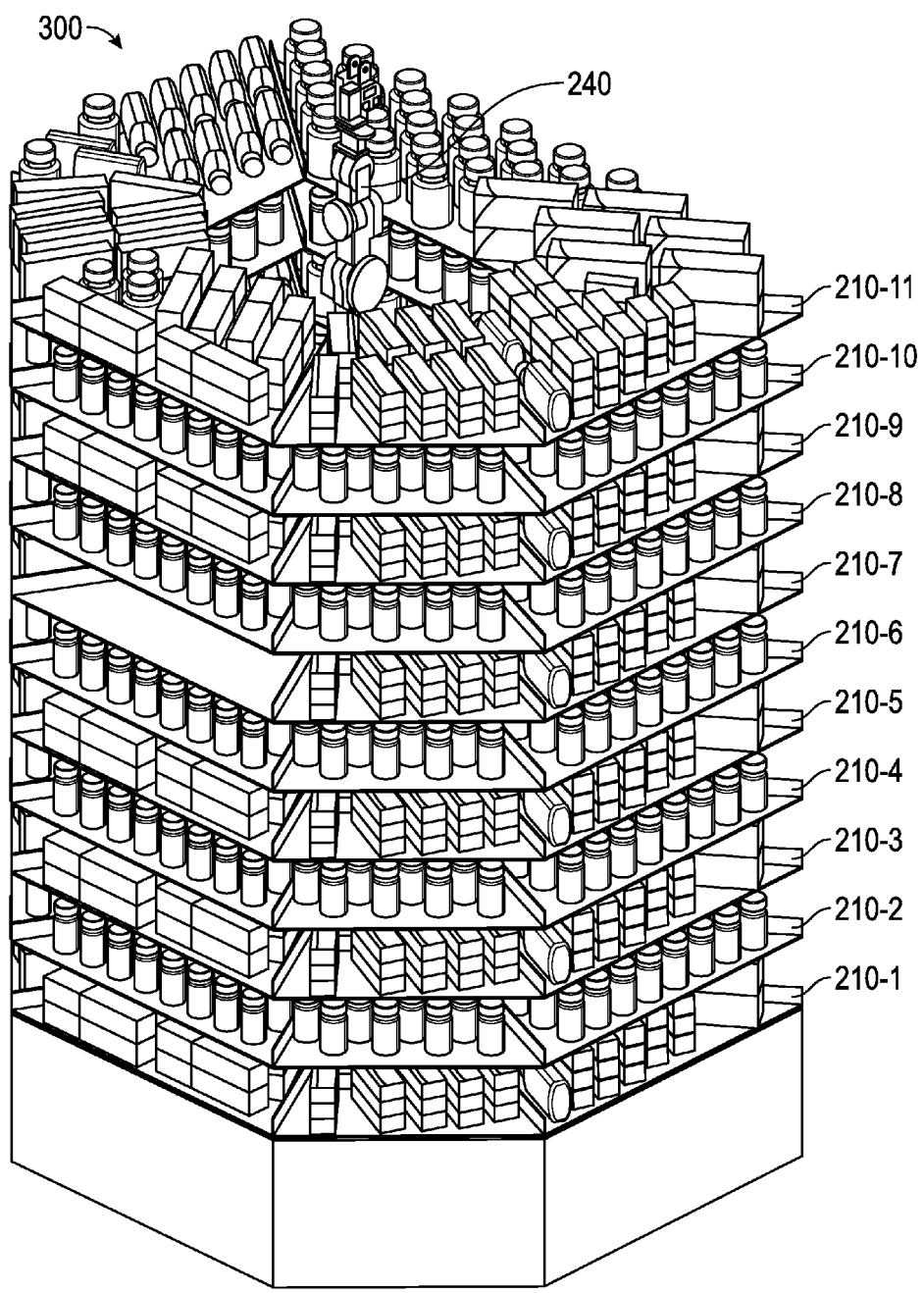
FIG. 13 illustrates a front angled view of the internal structure of a stocked medication-dispensing machine, according to an embodiment.
Figure 14:
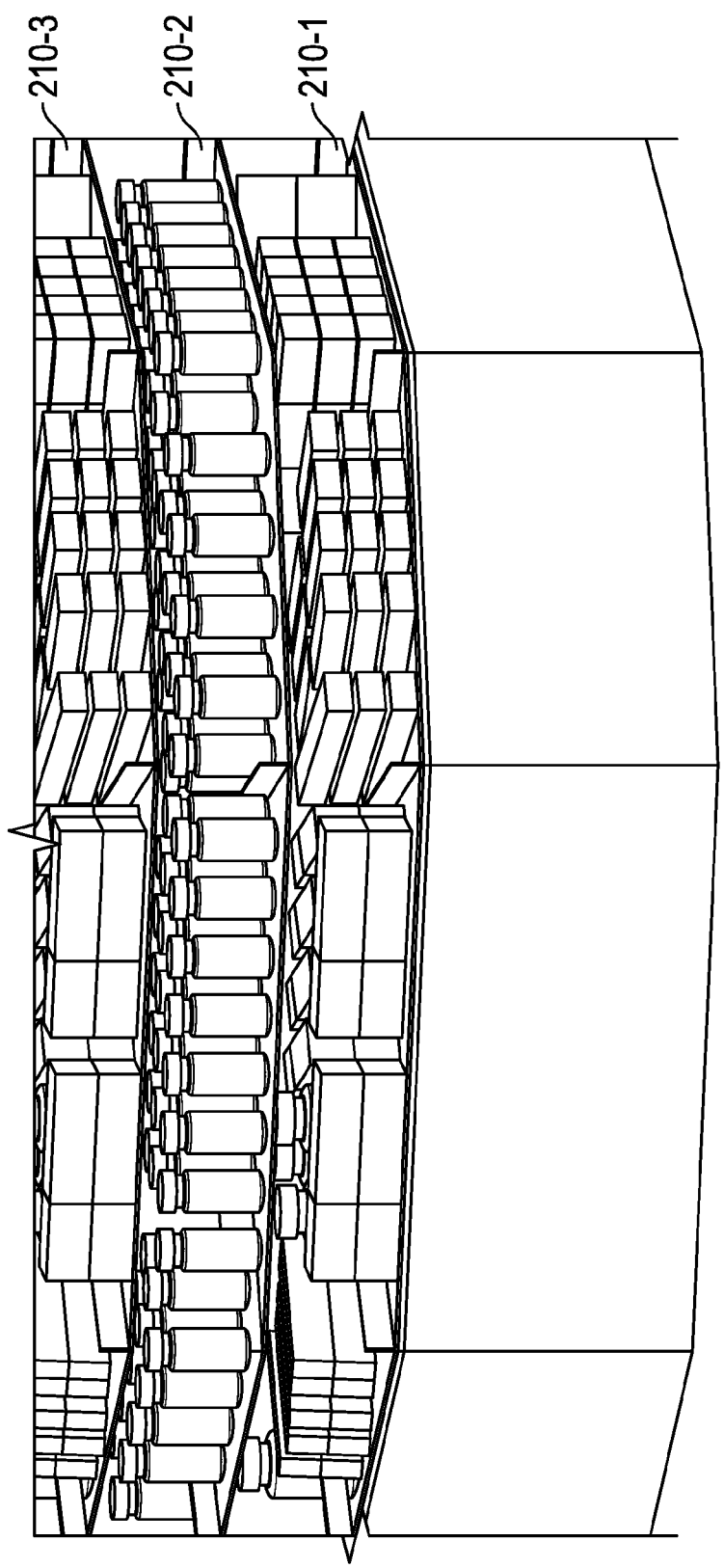
FIG. 14 illustrates a partial front view of the internal structure of a stocked medication-dispensing machine, including a lower restocking drawer, according to an embodiment.

FIGS. 7-10 illustrate internal structure 200 of medication-dispensing machine 100, depicted in FIGS. 5 and 6, from different perspectives. FIG. 7 is a cut-away view of internal structure 200 of machine 100 from a perspective of looking down at an angle from slightly above the machine. FIGS. 8 and 9 illustrate internal structure 200 of machine 100 from different side perspectives. FIG. 10 is a view of internal structure 200 of machine 100 from a top-down perspective.

FIGS. 11-14 illustrate different perspective views of an internal structure 300 of medication-dispensing machine 100 illustrated in FIGS. 1-4, according to an alternative to the embodiment illustrated in FIGS. 5-10. In this alternative embodiment, connection element 230 is positioned below mechanical arm 240, which extends upward from connection element 230. In contrast, in the embodiment of FIGS. 5-10, connection element 230 was positioned above mechanical arm 240, which extended downward from connection element 230. In addition, in the alternative embodiment of FIGS. 11-14, space is provided at the bottom of the machine, rather than at the top of the machine, in order to allow mechanical arm 240 to reach medication containers on the lowest platform (i.e., platform 210-1 in the illustrated embodiment).

Figure 15:
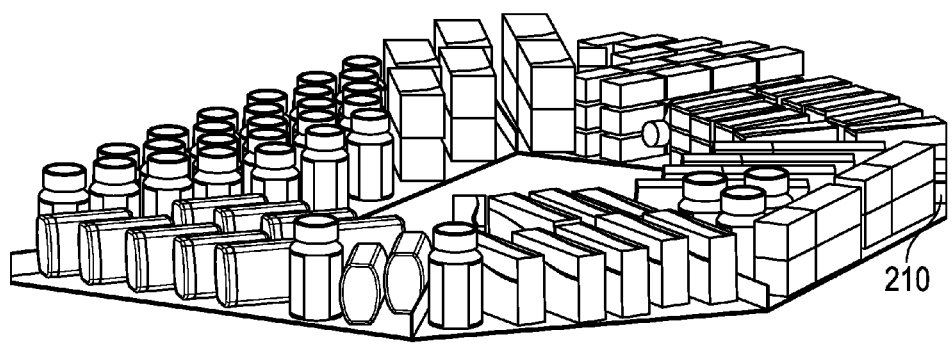
FIG. 15 illustrates a front angled view of a stocked medication-supporting platform for a medication-dispensing machine, according to an embodiment.
Figure 16:
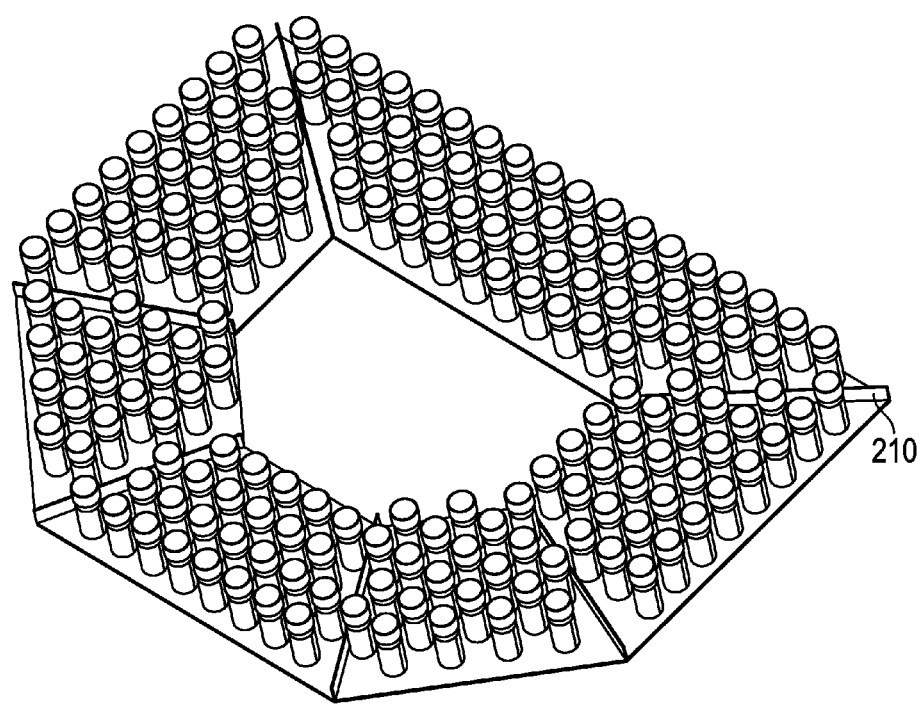
FIG. 16 illustrates an overhead angled view of a stocked medication-supporting platform for a medication-dispensing machine, according to an embodiment.
Figure 17:
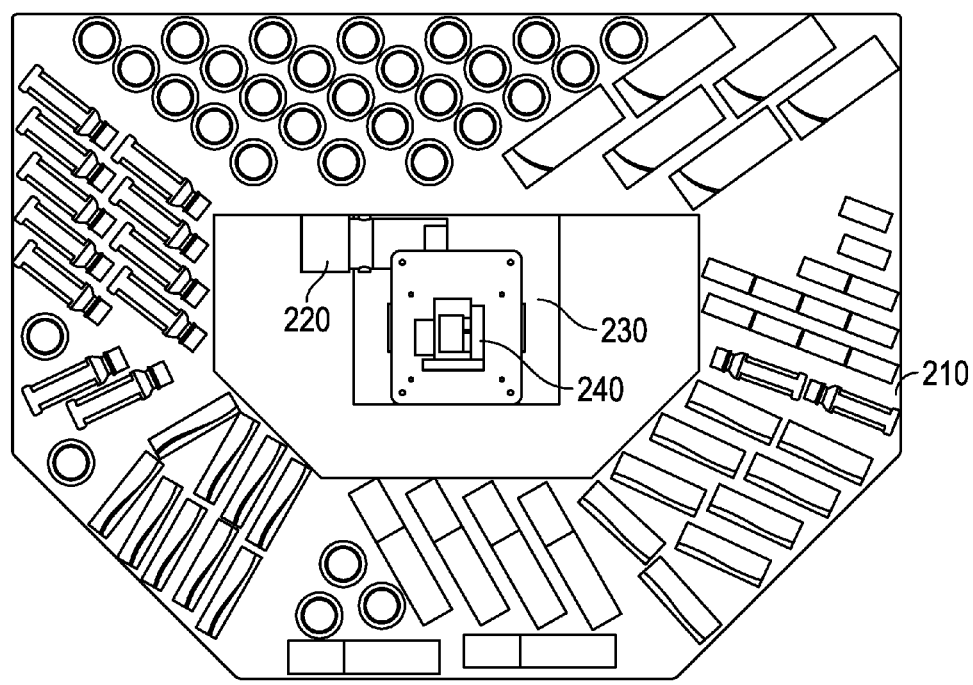
FIG. 17 illustrates an overhead view of a stocked medication-supporting platform for a medication-dispensing machine, according to an embodiment.

FIGS. 15-17 illustrate different perspective views of a platform 210, according to an embodiment. As illustrated, each platform 210 comprises a six-sided polygon. However, it should be understood that platforms 210 may comprise a polygon of any shape and any number of sides of three or more. Specifically, each platform may be configured in the same shape as the horizontal cross-section of the external covering of machine 100, which, as discussed above, may or may not be designed to angle multiple human-to-machine interfaces so as to increase privacy among users. Alternatively, different platforms 210 may comprise different shapes.

In an embodiment, each platform 210 comprises a central opening to accommodate shaft 220, connection element 230, and mechanical arm 240, as illustrated in FIG. 17. As discussed above, shaft 220 may be fixed to a portion of a side of the central opening for each, or for one or more, of platforms 210.

Furthermore, as illustrated, each platform 210 may be divided into a plurality of discrete sections, for example, using partial or full dividing walls or other dividing elements. For instance, in the embodiments illustrated in FIGS. 15 and 16, platform 210 is divided into six sections corresponding to the six external and internal sides of platform 210. However, it should be understood that platform 210 may comprise a different number of divisions, a different configuration of divisions, or no divisions at all. Furthermore, different platforms 210 may comprise different numbers of divisions.

As shown, containers of medication are stocked on platform 210 on the substrate between the outside borders of platform 210 and the inside borders formed by the central opening. Furthermore, in the embodiment in which platform 210 is divided into a plurality of discrete sections, the containers of medication may also be divided on platform 210 into the discrete sections. It should be understood that the containers of medication may be arranged in any suitable manner. For example, containers of medications may be divided between different platforms 210 and/or discrete sections of one or more platforms 210 according to medication type, brand, size, shape, etc. Alternatively or additionally, containers of medication may be arranged randomly throughout different platforms 210 and/or discrete sections of one or more platforms 210.

As discussed above, connection element 230 and/or mechanical arm 240 may be controlled to position claw 244 to grab containers of medication on any of platforms 210. Connection element 230 and mechanical arm 240 may be actuated using any conventional mechanical and/or electronic mechanisms for vertically driving an element up and down a shaft and rotating or otherwise moving joints. These mechanisms, as well as other mechanical and electronic mechanisms of medication-dispending machine 100 (e.g., displays or touch panels 110, dispensing enclosure 120, card reader 130, etc.) may be controlled by a processing device integral to or remote from machine 100, and described elsewhere herein according to an embodiment.

In an embodiment, the processing device of machine 100 may comprise system 550, described elsewhere herein, or components of system 550, according to the particular implementation. The processing device may be capable of communicating with one or more external systems (e.g., an Intelligent Pharmacy System (IPS) of the dispensary, web services, a user device, etc.) over one or more networks (e.g., an intranet, the Internet, etc.). For example, the processing device may be configured to establish an Internet-based session (e.g., web session, Voice over Internet Protocol (VoIP) session, etc.) or other type of session with a pharmacist via one or more communication channels (e.g., Internet, wireless communication network, telephone network, etc.). Additionally or alternatively, the processing device may be configured to communicate with and/or via an IPS that manages a dispensary or group of dispensaries.

In an embodiment, the processing device may be capable of imaging one or more internal areas of machine 100 using one or more internal cameras, and transmitting those images (e.g., as photographs or video) to one or more remote devices over one or more networks (e.g., an intranet, the Internet). For example, machine 100 may comprise one or more holding areas, and one or more of these holding areas may comprise a camera capable of producing a photograph or real-time video stream of a container of medication in the holding area. Alternatively or additionally, mechanical arm 240 may comprise a camera capable of imaging a container of medication on platform 210 or in a holding area within machine 100. In addition, mechanical arm 240 and/or one or more of the holding areas may comprise sensors capable of scanning a barcode and/or reading a Radio Frequency Identification (RFID) tag, and the processing device may be configured to process and/or transmit barcode information (e.g., information decoded from the barcode) or RFID information (e.g., information transmitted by an RFID tag) to one or more remote devices over one or more networks.

In an embodiment, the processing device may establish an audio or audiovisual session with a pharmacist. This session may be established using well-known protocols and/or applications (e.g., Skype™). The processing device may provide a real-time audio or audiovisual session by establishing a connection with a device of a pharmacist, technician, or other individual (e.g., home or office desktop or tablet, mobile phone, etc.) over one or more networks (e.g, the Internet, wireless communication network, telephone network, etc.) and/or via the IPS of the dispensary.

In an embodiment, the processing device may be configured to provide a virtual pharmacist to a user via display 110. The virtual pharmacist may comprise an application or module which renders a computer-generated avatar that is displayed on display 110 and that interacts with the user. The virtual pharmacist may welcome the user and make him or her feel comfortable, as well as provide information about prescription medication being released to the user, provide instructions regarding the dosage and how many times a day to take the medication, convey whether the medication needs to be taken with food or milk, discuss drug interactions, etc. In other embodiments, the virtual pharmacist may comprise artificial intelligence which interacts with the user using simple text inputs and outputs (e.g., via a touch panel provided with display 110).

In embodiments which utilize a virtual pharmacist, the processing device of machine 100 may be programmed with or have access to specific information (e.g., in a local or remote database) about each medication with which it is stocked. The virtual pharmacist module may be programmed to retrieve this information and present it to the user. It should be understood that in embodiments in which this information is stored locally, no remote connection may be necessary to provide the virtual pharmacist to the user. However, in embodiments which utilize the virtual pharmacist, the processing device of machine 100 may be capable of connecting the user with a live pharmacist (e.g., by establishing an audio or audiovisual session) upon request or in the event that the virtual pharmacist is unable to respond appropriately (e.g., the user asks a question which the virtual pharmacist is not programmed to answer).

The above paragraphs described several embodiments of a pharmaceutical vending machine. Those of ordinary skill in the art will recognize that certain components could be omitted and that other components could be added, including the substitution of certain components for other components, without departing from the scope of the invention.

Process for Dispensing Prescription Medication

Figure 18A:
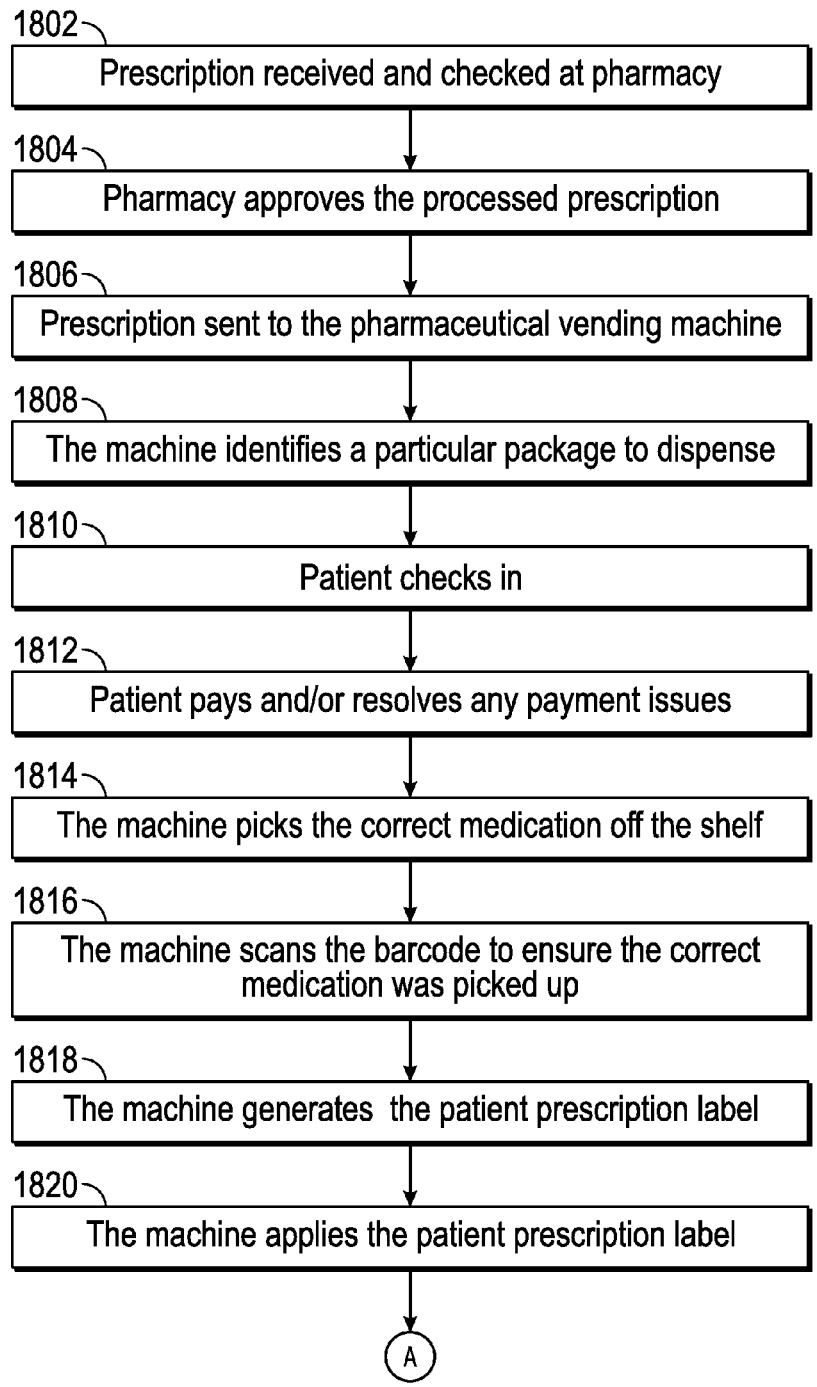
FIG. 18A illustrates a first set of steps for a process for dispensing prescription medication under the supervision of a pharmacist using a medication-dispensing machine, according to an embodiment.
Figure 18B:
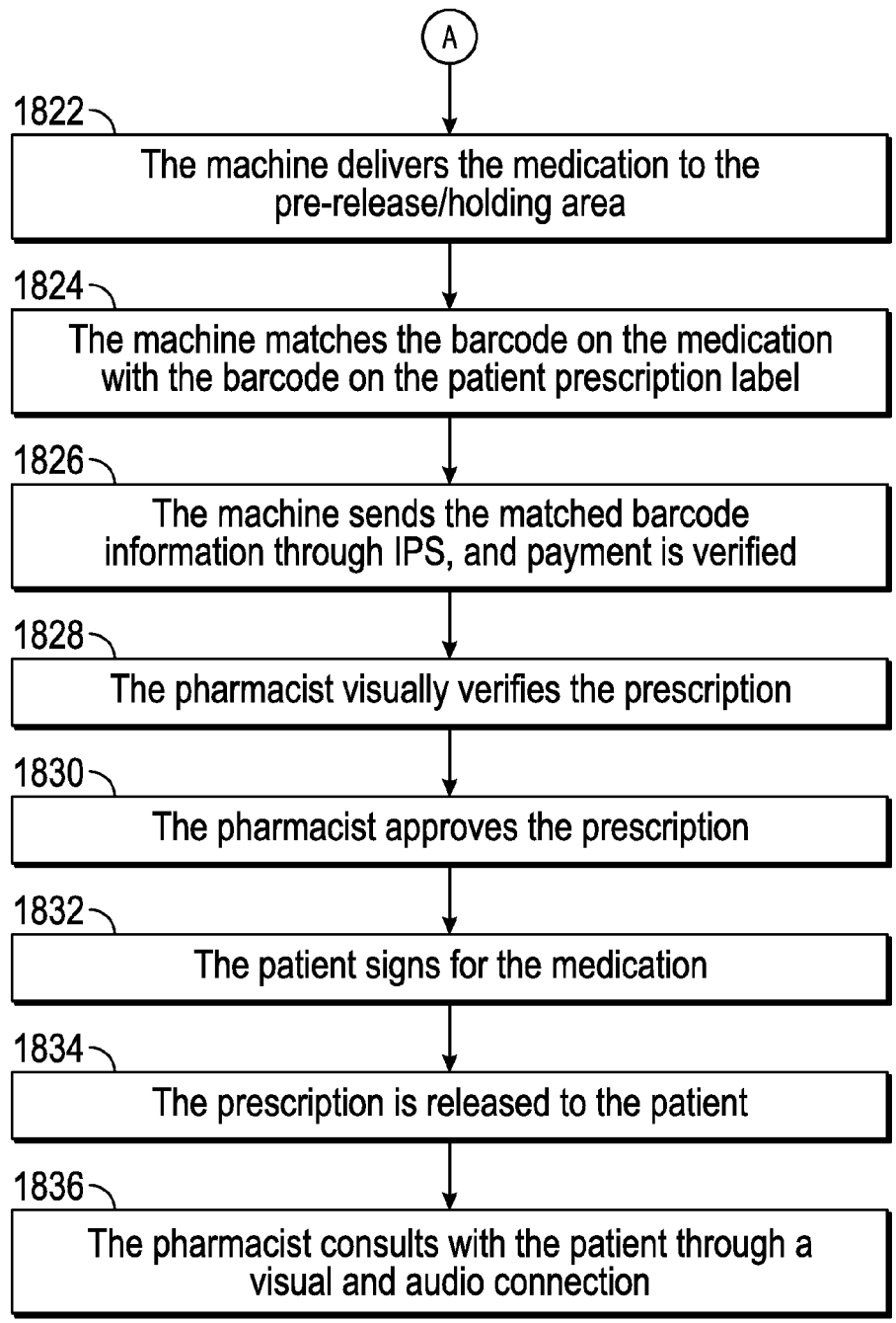
FIG. 18B illustrates a second set of steps for a process for dispensing prescription medication under the supervision of a pharmacist using a medication-dispensing machine, according to an embodiment.

A process, which utilizes a medication-dispensing machine, such as machine 100, in order to efficiently dispense prescription medication to a patient, will now be described with reference to FIGS. 18A and 18B, according to embodiments. It should be understood that the described embodiments are merely illustrative, and that the process may comprise fewer, more, or different combinations of steps than those described.

Initially, an electronic prescription may be input or otherwise specified by a doctor at the doctor's device (e.g., a computing device in the doctor's office). The electronic prescription may then be electronically transmitted to the dispensary via one or more networks (e.g., the Internet, wireless communication network, telephone network, etc.). For instance, the doctor may enter the electronic prescription into an electronic health record (EHR) database system, which then transmits it to a pharmacy across a network, such as the SureScripts™ Network.

Accordingly, in step 1802, the electronic prescription is received at a dispensary, such as a clinic or pharmacy. For example, the electronic prescription may be received at a patient's designated pharmacy using an IPS, such as the SuiteRx™ Intelligent Pharmacy System, or other system. After it has been received, the electronic prescription may be checked for accuracy, drug interactions, patient side effects, and/or issues with the formulary associated with the patient's health plan, and/or otherwise reviewed by the pharmacy's IPS, a module or application with which the IPS is interfaced or otherwise communicates, and/or by a person (e.g., technician, pharmacist, etc.).

In addition, the electronic prescription may be adjudicated for payment approval from the patient's health plan. For instance, an electronic claim may be automatically, semi-automatically, or manually generated and transmitted to an electronic claim-adjudication system for the patient's health plan (e.g., over one or more networks) that either denies or approves the claim. In response, an adjudication result (e.g., an approval or denial) may be received from the claim-adjudication system to which the electronic claim was submitted.

If the claim is approved, in step 1804, the electronic prescription may also be approved at the dispensary, for example, by a pharmacist. Notably, the electronic prescription may be reviewed and approved electronically, either automatically, semi-automatically, or manually, such that the review and approval may be performed remotely. Accordingly, a pharmacist does not have to be physically present at the dispensary in order to review and approve the prescription.

Once the electronic prescription has been approved at the dispensary, in step 1806, the electronic prescription may be transmitted to a medication-dispensing machine, such as machine 100. For example, the electronic prescription may be sent or relayed to a processing device in medication-dispensing machine 100 via the IPS (e.g., over one or more wired and/or wireless connections). Accordingly, the electronic prescription, or data extracted from the electronic prescription that identifies the prescribed medication, is received at the medication-dispensing machine.

In step 1808, a processing device of the medication-dispensing machine identifies a particular container of medication to dispense. For example, the machine may consult a database stored in a memory of the processing device or in a remote memory (e.g., over one or more networks) to identify a specific barcoded container of the prescription medication identified in information from the electronic prescription received at the machine. The database may comprise barcode information for each container of medication stocked inside the machine. This barcode information may be entered into the machine (e.g., manually or via a barcode scanner within the machine) at the time that each container is stocked within the machine. In addition, the medication-dispensing machine may transmit the barcode information (i.e., information encoded as or derived from a barcode on the identified container of medication to be dispensed) to or through the IPS, for example, for the purposes of storage, billing the patient's health plan, etc.

In an embodiment, the machine identifies particular containers of medication to be dispensed on a first-in first-out (FIFO) principle. In other words, from among a plurality of containers of the same medication stocked within the machine, the container of medication that has been present in the machine the longest is the first to be dispensed. Generally, this will reduce the possibility that a particular medication will expire while in the machine. However, it should be understood that other methods may be used to determine which particular container of medication to dispense (e.g., earliest expiration date, closest to mechanical arm 240, etc.).

In step 1810, an indication that the patient, or other user acting on behalf of the patient, has arrived at the location of the medication-dispensing machine is received. This indication may be received through an interaction with a human-to-machine interface of the medication-dispensing machine. For example, a user may input identifying information (e.g., name, identification code, confirmation code, etc.) into a touch panel or other input device of the human-to-machine interface. Alternatively, the user may input the identifying information in a terminal or other intermediary system (e.g., the IPS) which relays the identifying information and/or information derived from the identifying information to a medication-dispensing machine. As another alternative, the user may provide the identifying information to a technician or other personnel of the dispensary who inputs the information into the medication-dispensing machine or into the IPS which relays the information to the medication-dispensing machine.

In step 1812, after checking in with a medication-dispensing machine, the user may also pay for the prescription at the human-to-machine interface of the medication-dispensing machine. For example, the patient may swipe his or her credit card using card-reader 130 of machine 100 to pay any co-pay required by the patient's health plan. Alternatively, the patient may pay for the prescription at another terminal or through an interaction with a technician, in which case an indication of the payment may be provided to the medication-dispensing machine (e.g., via the IPS).

Furthermore, if any issues have arisen during the prescription approval process, such as billing or insurance issues (e.g., the claim for the electronic prescription was denied by the claim-adjudication system of the patient's health plan), the user may also resolve these issues at the time of check-in and/or payment. For example, the user may interact with a human-to-machine interface of the medication-dispensing machine, or a technician or terminal (e.g., of the IPS), to resolve any issues that would prevent the release of prescription medication and/or seek assistance in using the medication-dispensing machine.

In some embodiments, automated issue resolution and/or remote assistance may be provided via the touch panel of a human-to-machine interface of the medication-dispensing machine. For example, the touch panel display may prompt the user regarding unresolved issues and provide inputs which the user may utilize, for example, to answer questions or input information to resolve the issues. In addition, the machine may be able to connect the user with a remote pharmacist or technician, via a real-time text, audio, and/or video chat (e.g., using Skype™) over one or more networks (e.g., the Internet, a wireless communication network, a telephone network, etc.). In this manner, a user can interact with a person in real-time to resolve any issues or receive assistance in using the machine.

It should be understood that, while step 1808 has been illustrated as occurring before steps 1810 and 1812, step 1808 may occur after or at the same time as these steps. In other words, the medication-dispensing machine may identify the particular container of medication to be dispensed to the patient before, during, or after the patient has checked in and/or paid for the prescription. In addition, instead of consulting a database to identify a particular container of medication to dispense, machine 100 may consult a database to identify a location of a particular type of medication on one of platforms 210, select a container of medication from the identified location, and scan a barcode or other information on the container to identify the particular container of medication to be dispensed to the patient. This may performed as part of the process in step 1814, described below.

In step 1814, after the user has checked in and any issues that would prevent release of the prescription medication have been resolved, the medication-dispensing machine prepares the patient's prescription for dispensation. For example, medication-dispensing machine 100 may use its mechanical or robotic arm 240 and, in embodiments, its vision capabilities (e.g., one or more sensors) to select the correct container of medication from one of platforms 210.

In step 1816, the medication-dispensing machine scans a barcode or other information on the selected container of medication to verify that the correct medication has been selected. For example, claw 244 of mechanical arm 240 may grab the selected container of medication. Mechanical arm 240 may then carry the container of medication in claw 244 to a holding area within machine 100 for scanning. The barcode of the container of medication is then scanned in this scanning area to ensure that the correct medication was picked up. It should be understood that the term "barcode," as used herein, may be refer to any type of encoded information that can be printed on a container (e.g., one-dimensional barcode, two-dimensional barcode, Quick Response (QR) code, three-dimensional barcode, etc.). In an alternative embodiment, RFID may be used to identify containers of medication, rather than a barcode. In other word, each container of medication may comprise an RFID tag, and the machine may comprise an RFID reader capable of reading information (e.g., medication identification information) transmitted by the RFID tags.

Once it has been verified that the correct medication was picked up, in step 1818, the medication-dispensing machine generates a patient-specific prescription label. For example, a processing device of machine 100 may generate label data (e.g., by combining patient-specific data with a stored template). In an embodiment, the label data comprises a barcode that encodes information related to the patient, the prescription, the medication, the doctor who prescribed the medication, the patient's health plan, and/or the like.

In step 1820, the label is applied to the container of medication to be dispensed. For example, machine 100 may comprise an internal label printer which prints the generated label onto a physical label (e.g., adhesive-backed paper). In such an embodiment, mechanical arm 240 may pick up and/or orient the container in a printing area as needed so that the label may be evenly adhered to the container. Alternatively, the label may be applied to the container in a different manner. For instance, the container may be oriented towards the label printer (e.g., by mechanical arm 240 or other mechanical means) in a printing area of machine 100, and the label may be printed directly onto a standard or non-standard area of the container. In an embodiment, the label is applied to the container of medication such that a barcode on the container is not obscured.

In step 1822, the medication-dispensing machine delivers the selected and labeled container of medication to a pre-release holding area inside the machine. For example, mechanical arm 240 may pick up and carry the container of medication from the scanning and/or printing area to the holding area. Alternatively, the scanning and/or printing area(s) may be the same as or within the holding area, or some other mechanism may be provided to transport the container of medication between the different areas within the machine.

In an embodiment, the holding area initially prevents access to the container of medication. For example, the holding area may be separated from the outside of the machine by a lockable release door, which is initially locked. Dispensing enclosure 120 is an embodiment of the pre-release holding area. As illustrated a door is provided to prevent a patient from reaching into enclosure 120 and possessing a container of medication disposed therein prior to its release. The door may be opaque, translucent, or transparent. The door is capable of being opened and closed, and, in its closed state, may be automatically locked and unlocked (e.g., under the control of a processing device of machine 100). In addition, it should be understood that the opening and/or closing of the door may be automatic (e.g., under the control of a processing device of machine 100) or manual (e.g., by a user pushing or sliding the door when unlocked).

In step 1824, the medication-dispensing machine may scan the barcode on the container of medication to be dispensed to the patient, as well as the barcode on the label that was applied to the container of medication. This scanning process may be similar or identical to the scanning process described above, may take place in the scanning area of the holding area, and/or may utilize mechanical arm 240. A processing device of the machine may then compare information encoded in the two barcodes to ensure that they match, i.e., that the label was applied to the correct container of medication. This matching may comprise matching information encoded in both barcodes to each other. Alternatively, this matching may comprise matching first information contained in one of the barcodes to stored information (e.g., via an index of a relational database) and also matching second information in the other barcode to the same stored information (e.g., via an index of the relational database), thereby associating the first and second information to each other. If the two barcodes are mismatched, the medication-dispensing machine may perform failure processing, such as generating an alert, providing notification to a technician or pharmacist, retrieving a new container of medication to be labeled and dispensed, etc.

In step 1826, the medication-dispensing machine may transmit information from one or both of the scanned and matched barcodes and/or information derived from or associated with one or both of the scanned and matched barcodes to an external system, such as an IPS, for verification, billing, and/or tracking purposes. For instance, the IPS or other external system may verify payment, store data related to the transaction for tracking purposes, and/or the like.

In step 1828, a pharmacist may visually verify the prescription by viewing the container of medication in the holding area of the medication-dispensing machine. For instance, machine 100 may comprise an internal camera which is able to take a photograph or which provides real-time video of the container of medication as it sits in the holding area of dispensing enclosure 120. Machine 100 may then transmit the photograph or stream the video, over one or more networks, to the IPS or other external system (e.g., via an Internet connectivity platform, such as Skype™), such that the pharmacist may view the photograph or video on a terminal or on his or her own device (e.g., a home computer or mobile device). In an embodiment, machine 100 may comprise a web server which provides one or more user interfaces, comprising the photograph or video, over the Internet, for viewing by the pharmacist. The user interfaces may be interactive and may comprise inputs which allow the pharmacist to approve the dispensing of the container of medication, change a setting of the camera (angle, focus, etc.), and/or the like. In either case, the pharmacist does not need to be physically present at the dispensary in order to view and approve the container of medication that is to be released to the patient.

Prior to approving release of the container of medication to the user, the pharmacist may match one or more of the drug product (e.g., as determined by viewing the container of medication in the holding area), the National Drug Code (NDC) for the drug product, the label that has been applied to the container of medication (e.g., as determined by viewing the container of medication in the holding area, or by viewing information scanned from the barcode or otherwise derived from the label), and the original electronic prescription order from the patient's doctor. All or some of this information may be provided to the pharmacist in the same or similar manner as the photograph or video of the container of medication in the holding area of the medication-dispensing machine. For example, this information may be provided in the same user interface(s) as the photograph or video of the container of medication.

In step 1830, after the pharmacist has verified that the container of medication in the holding area of the medication-dispensing machine and all other information (e.g., on the applied patient label) is correct, the pharmacist may approve the container for release. For example, one or more inputs (e.g., buttons, icons, etc.) may be provided on the user interface(s) that have been provided to the pharmacist (e.g., by the medication-dispensing machine and/or IPS) for viewing the container of medication in the holding area, or may be provided on other user interfaces (e.g., provided by the IPS) which interact with the medication-dispensing machine (e.g., directly or via the IPS) and enable the pharmacist to approve the release of the container of medication to the user.

In step 1832, the user may be required to sign for the medication. For example, a touch panel of display 110 or other input of the human-to-machine interface of machine 100 may prompt the user to sign the touch panel (e.g., using his or her finger or a provided stylus). The user may be required or prompted to read instructions and/or make certain acknowledgments (e.g., acknowledgement that the user has read the usage instructions, acknowledgement of risks or side effects, etc.) prior to or via his or her signature. The user's signature may be captured by the medication-dispensing machine and stored (e.g., in the medication-dispensing machine, or transmitted to and stored in the IPS) for tracking purposes.

In step 1834, once the pharmacist has approved the container of medication for release, payment (if applicable) has been approved, and the user has signed for the medication (if applicable), the medication-dispensing machine may unlock and/or open the secure release door of dispensing enclosure 120. In an embodiment, the door of dispensing enclosure 120 will not unlock or open until all three of these conditions have been met (i.e., approval, payment, and signature). Once the door has been unlocked or opened, the user may reach into dispensing enclosure 120 and retrieve the container of medication.

In step 1836, the pharmacist may consult with the patient through an audio or audiovisual session, such as through Skype™. Specifically, the medication-dispensing machine may provide a real-time audio or audiovisual session by connecting the medication-dispensing machine with a device of the pharmacist (e.g., home or office desktop or tablet, mobile phone, etc.) over one or more networks, such as the Internet. The connection may be provided via the IPS of the dispensary or directly between the machine and a device of the pharmacist, and, in some embodiments, the session may be recorded. It should be understood that step 1836 may occur at any time after the user begins a session with the medication-dispensing machine (e.g., in step 1810), including simultaneously with any of steps 1808-1834.

During an audiovisual session, the touch panel or display 110 of the human-to-machine interface of medication-dispensing machine 100 may provide a real-time video image of the pharmacist. In addition, speakers of the human-to-machine interface may provide real-time audio of the pharmacist's speech. Furthermore, an externally-facing camera and microphone of the human-to-machine interface may collect real-time video and audio of the user, and transmit this data to the pharmacist. It should be understood that an audio-only connection may be implemented in a similar manner, but without the need for the externally-facing camera and without displaying real-time video of the pharmacist on display 110.

During the audio or audiovisual session between the user and pharmacist, the pharmacist may speak directly to the user and vice versa. For instance, the pharmacist may provide information or instructions about the medication being dispensed, answer the user's questions, ask the user questions, etc. Similarly, the user may ask the pharmacist questions, answer the pharmacist's questions, etc. This direct connection between the pharmacist and user can aid in pharmacist-patient bonding, which may, in turn, improve the rate of medication adherence, as well as improve customer loyalty.

In an alternative embodiment, a virtual pharmacist may be presented to the user, as discussed above, rather than an actual pharmacist. However, in embodiments which utilize the virtual pharmacist, the medication-dispensing machine may be capable of connecting the user with a live pharmacist (e.g., in the manner described above) upon request or in the event that the virtual pharmacist is unable to respond appropriately (e.g., the user asks a question which the virtual pharmacist is not programmed to answer).

The above steps describe one possible embodiment of a process for using a pharmaceutical vending machine. Those of ordinary skill in the art will recognize that certain steps could be omitted or performed in a different order or simultaneously with other steps, and that other steps could be added, without departing from the scope of the invention.

Example System Infrastructure

Figure 19:
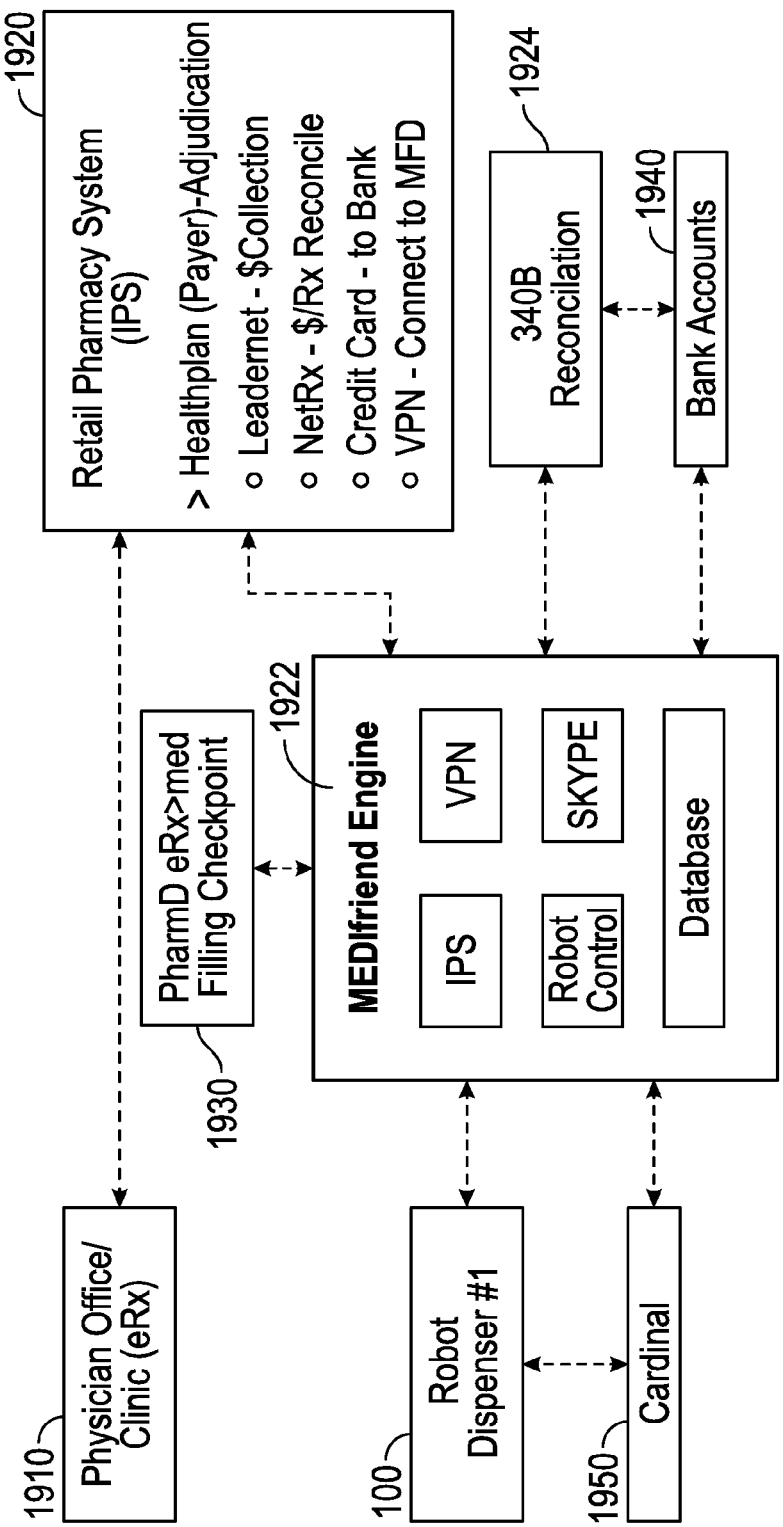
FIG. 19 illustrates components and relationships of a system infrastructure in which a medication-dispensing machine may operate, according to an embodiment.

An infrastructure for a system that includes a medication-dispensing machine, such as machine 100, and which may support the process described above with respect to FIGS. 18A and 18B, will now be described. FIG. 19 illustrates such a system infrastructure, according to an embodiment. It should be understood that the various components may communicate in a bidirectional or unidirectional manner using any standard or proprietary protocol(s).

Initially, a physician's or clinic's system 1910 may receive an electronic prescription for a patient. In an embodiment, this electronic prescription is transmitted to IPS 1920 of a dispensary, such as a pharmacy. IPS 1920 may comprise one or more of a health plan adjudication module, a collections module, a reconciliation module, and a payment module. The health plan adjudication module may interact with a claim-adjudication system for the patient's health plan in order to submit and receive approval or denial of a claim. The collections module may facilitate claim management and reimbursement. The reconciliation module may provide reconciliation for collections and payments. The payment module may initiate or process customer transactions, such as credit or debit card transactions (e.g., through a third-party).

In addition, IPS 1920 may comprise or be interfaced or otherwise connected with an engine 1922 (e.g., via a Virtual Private Network (VPN)) for facilitating or implementing the processes described herein. Engine 1922 may comprise one or more modules that provide an interface between IPS 1920 and medication-dispensing machine 100. Engine 1922 may also interface with other systems, such as a medication filing checkpoint 1930 for validating an electronic prescription (e.g., in step 1802 of the process illustrated in FIG. 18A), a 340B reconciliation system 1924 for managing 340B programs, one or more bank accounts 1940, and/or one or more health management systems 1950 (e.g., Cardinal Health™). In embodiments, 340B reconciliation system 1924 may also communicate directly with bank accounts 1940, and medication-dispensing machine 100 may communicate directly with the health management system(s) 1950.

In an embodiment, engine 1922 comprises a control module that provides control commands to machine 100. For example, the module may instruct machine 100 to retrieve and prepare the prescription medication from an electronic prescription (e.g., using mechanical arm 240), scan one or more containers of medication in machine 100, apply a patient label, scan a patient label, release medication in dispensing enclosure 120, and the like. The module may also interface with machine 100 to receive information from machine 100, such as scanned barcode information from containers of medication and/or applied patient labels, payment information, requests for approval to release a container of medication, requests to establish an audio or audiovisual session between a user and pharmacist or technician, etc., as well as act as an interface between machine 100 and IPS 1920 (e.g., via a first interface to machine 100 and a second interface to IPS 1920) and one or more other components of the infrastructure. Engine 1922 may also comprise or have access to a database for storing data used or acquired during its operation.

In an embodiment, engine 1922 may comprise a module or application for establishing an audio or audiovisual session between machine 100 and a remote device (e.g., desktop or mobile device, not shown), such that a user of machine 100 and a pharmacist or other user of the remote device can converse. For example, engine 1922 may use Skype™ or another VoIP service to establish the audio or audiovisual session.

Example Processing Device

Figure 20:
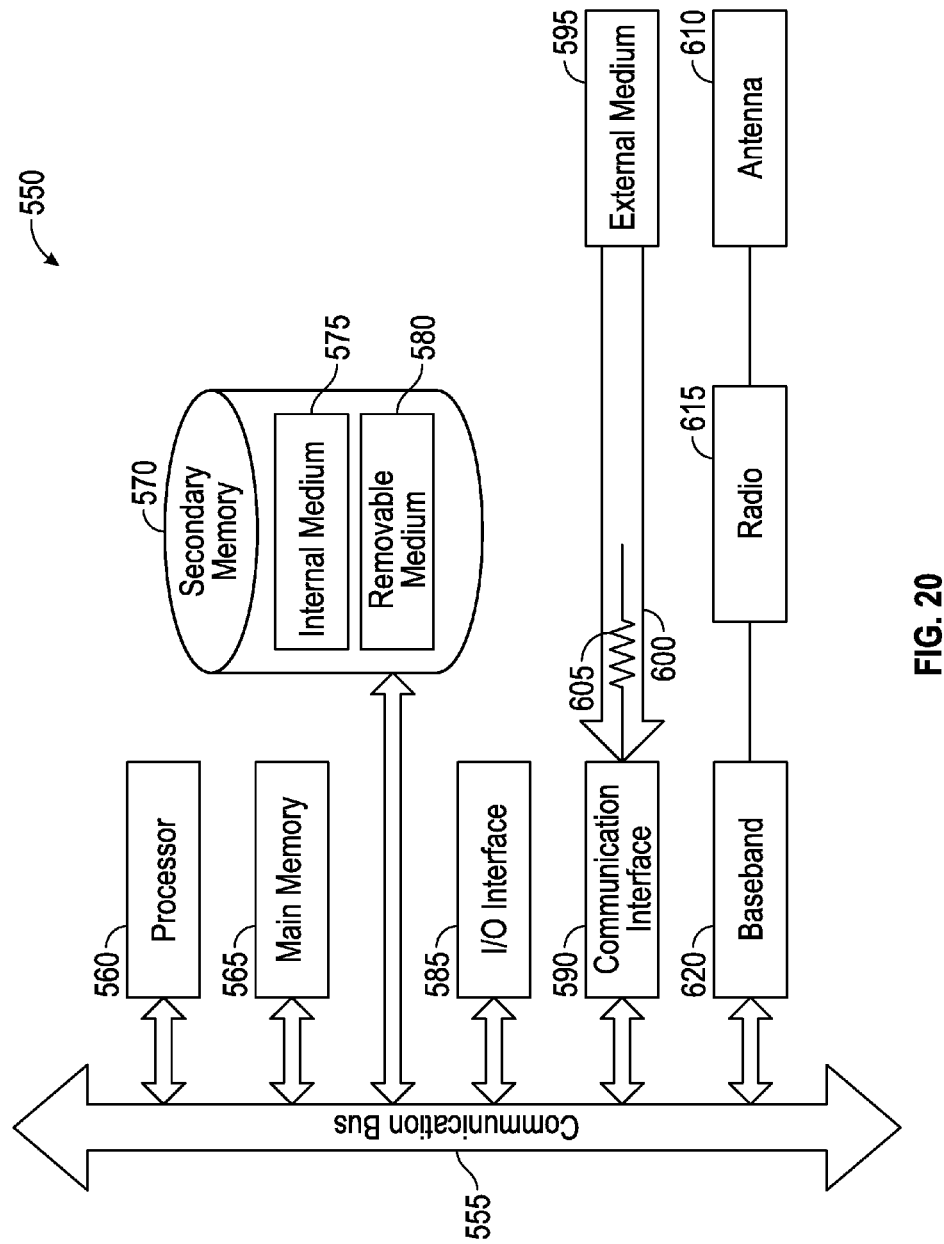
FIG. 20 illustrates an example processing system on which one or more functions of the processes described herein may be executed, according to an embodiment.

FIG. 20 is a block diagram illustrating an example wired or wireless system 550 that may be used in connection with various embodiments described herein. For example the system 550 may be used as or in conjunction with one or more of the mechanisms, processes, methods, or functions described above, and may represent components of medication-dispensing machine 100, such as the processing device of machine 100 discussed above. The system 550 can be a server or any conventional personal computer, or any other processor-enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560. Examples of processors which may be used with system 550 include, without limitation, the Pentium® processor, Core i7® processor, and Xeon® processor, all of which are available from Intel Corporation of Santa Clara, Calif.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

System 550 preferably includes a main memory 565 and may also include a secondary memory 570. The main memory 565 provides storage of instructions and data for programs executing on the processor 560, such as one or more of the functions and/or modules discussed above. It should be understood that programs stored in the memory and executed by processor 560 may be written and/or compiled according to any suitable language, including without limitation C/C++, Java, JavaScript, Perl, Visual Basic, .NET, and the like. The main memory 565 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The secondary memory 570 may optionally include an internal memory 575 and/or a removable medium 580, for example a floppy disk drive, a magnetic tape drive, a compact disc (CD) drive, a digital versatile disc (DVD) drive, other optical drive, a flash memory drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer-readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 590. Examples of external storage medium 595 may include an external hard disk drive or an external optical drive, or and external magneto-optical drive.

Other examples of secondary memory 570 may include semiconductor-based memory such as programmable read-only memory (PROM), erasable programmable read-only memory (EPROM), electrically erasable read-only memory (EEPROM), or flash memory (block-oriented memory similar to EEPROM). Also included are any other removable storage media 580 and communication interface 590, which allow software and data to be transferred from an external medium 595 to the system 550.

System 550 may include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device.

Communication interface 590 preferably implements industry promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

In an embodiment, I/O interface 585 provides an interface between one or more components of system 550 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

The system 550 also includes optional wireless communication components that facilitate wireless communication over a voice and over a data network. The wireless communication components comprise an antenna system 610, a radio system 615 and a baseband system 620. In the system 550, radio frequency (RF) signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown).

Various embodiments may also be implemented primarily in hardware using, for example, components such as application specific integrated circuits (ASICs), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA, or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the general principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A method for dispensing prescription medication, the method comprising using at least one hardware processor of a medication-dispensing machine to: receive an identification of medication and patient information for an electronic prescription; retrieve a container of the identified medication from a plurality of containers of medication that are stocked within the medication-dispensing machine, wherein each of the plurality of containers of medication comprises a first barcode; scan the first barcode of the retrieved container; generate a patient label based on at least the patient information; apply the patient label to the retrieved container; capture an image of the labelled container, wherein the captured image shows the retrieved container and the patient label; provide the captured image and the electronic prescription over at least one network to a remote pharmacist; receive approval over the at least one network from the remote pharmacist based on at least a visual inspection of the captured image and the electronic prescription by the remote pharmacist; wherein the visual inspection comprises matching the retrieved container, the patient information on the patient label, and the electronic prescription, and, based on the approval, release the labelled container to a user.

2. The method of claim 1, wherein the applied patient label comprises a second barcode, and wherein the method further comprises using the at least one hardware processor to, prior to releasing the retrieved container to the user: scan the first barcode on the retrieved container and the second barcode on the applied patient label; and confirm that data encoded in the first barcode corresponds to data encoded in the second barcode.

3. The method of claim 1, wherein the medication-dispensing machine comprises a display, and wherein the method further comprises using the at least one hardware processor to establish real-time communication, over the at least one network, between the user and the pharmacist via the display.

4. The method of claim 1, wherein the medication-dispensing machine comprises a dispensing enclosure with a door that can be switched between a locked state and an unlocked state, wherein the method further comprises using the at least one hardware processor to place the retrieved container within the dispensing enclosure while the door is in a locked state, and wherein releasing the retrieved container to the user comprises switching the door to an unlocked state.

5. The method of claim 1, further comprising using the at least one hardware processor to receive a signature from the user, wherein releasing the retrieved container to the user is further based on receiving the signature from the user.

6. The method of claim 1, further comprising using the at least one hardware processor to receive a payment for the identified medication from the user, wherein releasing the retrieved container to the user is further based on the payment.

7. The method of claim 1, wherein the plurality of containers of medication comprise a plurality of subsets of one or more containers of medication, and wherein each of the plurality of subsets comprises a container having a different size or shape than other ones of the plurality of subsets.

8. The method of claim 1, wherein retrieving the container of the identified medication comprises controlling a mechanical arm, comprising one or more joints and a claw, to grab the container of the identified medication from a platform within the medication-dispensing machine, wherein the platform supports a plurality of containers of medication.

9. The method of claim 1, further comprising using the at least one hardware processor to receive an identification of the user from the user, wherein retrieving the container of the identified medication is performed after receiving the identification of the user.

10. The method of claim 1, wherein the captured image comprises one of a photograph and a video.

11. A medication-dispensing machine comprising: at least one hardware processor; a mechanical device for retrieving a container of medication from a plurality of containers of medication that are stocked within the medication-dispensing machine, wherein each of the plurality of containers of medication comprise a first barcode; a dispensing enclosure comprising a door which can be switched between a locked state and an unlocked state; and one or more executable modules that, when executed by the at least one hardware processor, receive an identification of medication and patient information for an electronic prescription, control the mechanical device to retrieve a container of the identified medication from the plurality of containers of medication and place the retrieved container within the dispensing enclosure while the door is in the locked state, control a barcode scanner to scan the first barcode of the retrieved container, generate a patient label based on at least the patient information, apply the patient label to the retrieved container, control a camera to capture an image of the labelled container, wherein the captured image shows the retrieved container and the patient label, provide the captured image and the electronic prescription over at least one network to a remote pharmacist, receive approval over the at least one network from the remote pharmacist based on at least a visual inspection of the captured image and the electronic prescription by the remote pharmacist, wherein the visual inspection comprises matching the retrieved container, the patient information on the patient label, and the electronic prescription, and, based on the approval, release the labelled container to a user by at least switching the door of the dispensing enclosure to the unlocked state.

12. The medication-dispensing machine of claim 11, wherein the applied patient label comprises a second barcode, and wherein the one or more executable modules are further configured to, prior to releasing the retrieved container to the user: control the barcode scanner to scan the first barcode on the retrieved container and the second barcode on the applied patient label; and confirm that data encoded in the first barcode corresponds to data encoded in the second barcode.

13. The medication-dispensing machine of claim 11, further comprising a display, and wherein the one or more executable modules are further configured to establish real-time communication, over the at least one network, between the user and the pharmacist via the display.

14. The medication-dispensing machine of claim 13, wherein the real-time communication comprises audio and video.

15. The medication-dispensing machine of claim 11, further comprising a touch panel, wherein the one or more executable modules are further configured to receive a signature from the user via the touch panel, and wherein releasing the retrieved container to the user is further based on receiving the signature from the user.

16. The medication-dispensing machine of claim 11, wherein the one or more executable modules are further configured to receive a payment for the identified medication from the user, and wherein releasing the retrieved container to the user is further based on the payment.

17. The medication-dispensing machine of claim 11, wherein the plurality of containers of medication comprise a plurality of subsets of one or more containers of medication, and wherein each of the plurality of subsets comprises a container having a different size or shape than other ones of the plurality of subsets.

18. The medication-dispensing machine of claim 11, further comprising one or more platforms, wherein each of the one or more platforms supports a plurality of containers of medication, wherein the mechanical device comprises a mechanical arm comprising one or more joints and a claw, and wherein controlling the mechanical device to retrieve a container of the identified medication comprises controlling the mechanical arm to grab the container of the identified medication from one of the one or more platforms.

19. The medication-dispensing machine of claim 11, wherein the one or more executable modules are further configured to receive an identification of the user from the user, and wherein the one or more executable modules control the mechanical device to retrieve the container of the identified medication after receiving the identification of the user.

20. The medication-dispensing machine of claim 11, wherein the captured image comprises one of a photograph and a video.

* * * * *